US008862221B2

(12) United States Patent
Blomqvist

(10) Patent No.: US 8,862,221 B2
(45) Date of Patent: Oct. 14, 2014

(54) MONITORING MECHANICAL HEART PROPERTIES

(75) Inventor: Andreas Blomqvist, Spånga (SE)

(73) Assignee: St. Jude Medical AB, Jarfalla (SE)

( * ) Notice: Subject to any disclaimer, the term of this patent is extended or adjusted under 35 U.S.C. 154(b) by 1470 days.

(21) Appl. No.: 12/526,177

(22) PCT Filed: Feb. 21, 2007

(86) PCT No.: PCT/SE2007/000155
§ 371 (c)(1),
(2), (4) Date: Aug. 6, 2009

(87) PCT Pub. No.: WO2008/103078
PCT Pub. Date: Aug. 28, 2008

(65) Prior Publication Data
US 2010/0324442 A1     Dec. 23, 2010

(51) Int. Cl.
*A61B 5/053* (2006.01)
*A61B 5/08* (2006.01)
*A61N 1/365* (2006.01)
A61B 5/042 (2006.01)
A61B 5/145 (2006.01)

(52) U.S. Cl.
CPC ........... *A61N 1/36521* (2013.01); *A61B 5/0422* (2013.01); *A61B 5/145* (2013.01); *A61B 5/0538* (2013.01); *A61B 5/0535* (2013.01); *A61B 5/0809* (2013.01)
USPC ........... 600/547; 600/481; 600/483; 600/508; 600/509; 600/529

(58) Field of Classification Search
USPC ......... 600/481, 483, 484, 508, 509, 513, 547; 607/17
See application file for complete search history.

(56) References Cited

U.S. PATENT DOCUMENTS

| 5,282,840 | A | 2/1994 | Hudrlik |
| 6,473,640 | B1 | 10/2002 | Erlebacher |
| 7,190,996 | B2 | 3/2007 | Järverud |
| 7,308,309 | B1 * | 12/2007 | Koh ............................... 607/17 |
| 7,430,447 | B2 * | 9/2008 | Min et al. ....................... 607/17 |
| 8,135,463 | B2 * | 3/2012 | Burnes et al. .................... 607/9 |
| 2003/0204212 | A1 | 10/2003 | Burnes et al. |
| 2006/0276848 | A1 | 12/2006 | Min et al. |

FOREIGN PATENT DOCUMENTS

WO    WO 01/03580    1/2001

OTHER PUBLICATIONS

M. Brennan, M. Palaniswami, P. Kamen. Do Existing Measures of Poincaré Plot Geometry Reflect Nonlinear Features of Heart Rate Variability? Nov. 20001. IEEE Transaction on Biomedical Engineering vol. 48 No. 11 pp. 1342-1346.*

* cited by examiner

*Primary Examiner* — Navin Natnithithadha
*Assistant Examiner* — Meredith Weare

(57) ABSTRACT

In a method and system for monitoring mechanical properties of a heart in a subject, multiple cardiogenic impedance values reflective of the impedance of the heart in connection with a transition from inhalation to exhalation in the subject are determined. Correspondingly, multiple cardiogenic impedance values reflective of the impedance of the heart in connection with a transition from exhalation to inhalation are determined. The impedance values are collectively processed to form a trend parameter. The value determination and processing is performed over several respiratory cycles spaced apart in time to form a plurality of trend parameters over time. The mechanical properties of the heart are monitored by processing these different trend parameters. The data collection and optionally at least a part of the data processing is performed by an implantable medical device.

22 Claims, 15 Drawing Sheets

MONITORING MECHANICAL HEART PROPERTIES

BACKGROUND OF THE INVENTION

1. Field of the Invention

The present invention generally relates to heart monitoring, and in particular to methods and devices for monitoring the mechanical properties of the heart.

2. Description of the Prior Art

The heart is an essential organ in humans and most animals, pumping blood throughout the human/animal body. As a consequence, it is fundamentally important that the mechanical pumping properties of the heart operate correctly.

There are several diseases and conditions that negatively affect these mechanical properties of the heart, including cardiac ischemia. Cardiac ischemia is a condition where the flow of oxygen-rich blood to the heart muscle is restricted. This form of ischemia occurs when an artery becomes narrowed or blocked for a short time, preventing oxygen-rich blood from reaching the heart. If ischemia is severe or lasts too long, it can cause a heart attack (myocardial infarction) and can lead to heart tissue death. In most cases, a temporary blood shortage to the heart causes pain of angina pectoris. This will then be an indication to the patient that something is not right and he/she should contact a physician.

However, in other cases, there is no pain. These cases are called silent ischemia in the art. This is a severe condition as the patient may not notice that an ischemic condition has occurred or is present and will therefore not contact a physician.

The American Heart Association estimates that 3 to 4 million Americans have episodes of silent ischemia. People who have had previous heart attacks or those who have diabetes are especially at risk for developing silent ischemia. Heart muscle disease (cardiomyopathy) caused by silent ischemia is among the more common causes of heart failure in the United States.

Today there are two main tests that can be used to diagnose silent ischemia. Firstly, an exercise stress test can show blood flow through the coronary arteries in response to exercise, usually walking on a treadmill. Secondly, Holter monitoring records the heart rate and rhythm over at least a 24-hour period. The patient wears a recording device, the Holter monitor, which is connected to disks on the chest. A physician can then look at the printout of the recording to find out if the patient has had episodes of silent ischemia while he/she was wearing the Holter monitor.

However, these two tests require the active participation of a physician. The Holter monitoring is further limited as episodes of silent ischemia must occur during the actual monitoring and previous episodes of ischemia may remain unnoticed. In addition, it is highly unlikely that a patient suffering from attacks of silent ischemia indeed will contact a physician and undergo one of the prior art tests. As silent ischemia seldom has any symptoms, the patient is not aware of the deleterious condition and will therefore not visit a physician.

There are also other conditions and diseases that affect the mechanical properties of the heart in addition to ischemia. For example, heart infarcts cause necrosis of the heart tissue, poor inter-chamber synchronization will cause remodulation while other heart failures can lead to increased heart size (hypertrophy).

The document EP 1 384 433 discloses an apparatus for early detection of an ischemic heart disease. The apparatus comprises means for measuring an intracardiac impedance of a patient's heart and generating a corresponding impedance signal. A notch detector is provided for detecting the occurrence of a notch in the impedance signal coincident with the entry of blood into the ventricle. The apparatus also comprises a pattern recognition means for comparing the measured post-notch impedance curve with a stored predetermined reference impedance curve template to detect an ischemic heart disease.

There is therefore a need for a monitoring of the mechanical properties of the heart that can be used for detecting ischemia or another heart disease or condition affecting these properties. In particular, such monitoring should be able to also detect of silent ischemia and other unnoticed heart failures.

SUMMARY OF THE INVENTION

The present invention overcomes these and other drawbacks of the prior art arrangements.

It is a general object of the present invention to provide a monitoring of mechanical properties of the heart of a subject.

It is a particular object of the invention to provide a heart property monitoring that could be used in connection with heart diagnosing.

It is another particular object of the invention to provide a heart property monitoring useful in detecting silent ischemia and other unnoticed heart failures.

These and other objects are met by the invention as defined by the accompanying patent claims.

Briefly, the present invention involves methods, devices and systems for monitoring mechanical properties of a heart in a subject, preferably mammalian subject and more preferably a human subject.

The monitoring involves determining a first set of multiple cardiogenic impedance values of the subject. These impedance values are reflective of the impedance of the subject's heart in connection with a transition from inhalation to exhalation in the subject. In other words, these impedance values reflect the cardiogenic impedance at or near maximum lung volume or inflation. Correspondingly, a second set of multiple cardiogenic impedance values are also determined. These values are reflective of the impedance of the heart in connection with a transition from exhalation to inhalation in the subject. The values are, thus, reflective of the cardiogenic impedance at or near minimum lung volume.

The impedance values in these two sets are collectively processed to form or generate a trend parameter. This trend parameter will be an indication or estimate of the difference in cardiogenic impedance at different occasions in the respiratory cycle. The determination of the cardiogenic values in connection with subject exhalation and inhalation are performed during several such exhalation-inhalation and inhalation-exhalation transitions. Each such set pair (first and second set) is then collectively processed to form trend parameters. The result of these multiple data processings is thus a plurality of trend parameters over times.

The mechanical properties of the subject's heart are monitored by processing the plurality of trend parameters. This processing may, for example, include plotting the trend parameters in a diagram versus time to allow detection of any sudden change in the parameter values, which may be an indication of a deleterious change in the mechanical properties of the subject's heart.

In a preferred implementation, impedance measurements are used not only for determining the cardiogenic impedance values employed for generating the trend parameters. Impedance values representative of the respiratory impedance of the subject can be used for identifying when the transitions between inhalation/exhalation and exhalation/inhalation occur. This means that this respiratory impedance is useful for identifying when cardiogenic impedance measurements should be performed or for identifying those cardiogenic impedance values that coincidence with or fall close to a respiration transitions.

The measurement of the cardiogenic and the preferred respiratory impedance used in the monitoring of the present invention is preferably performed by an implantable medical device, e.g. pacemaker, cardiac defibrillator or cardioverter, implanted in the subject. Correspondingly, at least a portion of the data processing conducted in the monitoring of the invention may be implemented in the implantable medical device. Alternatively, or in addition, the data processing is performed by an external device in wireless communication with the implantable medical device based on raw data or partly processed data from the implanted device. In such a case, this external device can trigger an alarm notifying the subject or a physician if the mechanical property monitoring of the invention detects any deleterious heart condition.

The invention offers the following advantages:

Can be used in connection with early detection of deleterious heart conditions affecting the mechanical heart properties;

Allows detection of silent and symptom-free conditions such silent ischemia; and Can be implemented using traditionally employed impedance-measuring equipment.

Other advantages offered by the present invention will be appreciated upon reading of the below description of the embodiments of the invention.

BRIEF DESCRIPTION OF THE DRAWINGS

FIG. 20 is a schematic block diagram illustrating an embodiment of the impedance calculator of FIG. 19 in more detail.

DESCRIPTION OF THE PREFERRED EMBODIMENTS

Figure 1:
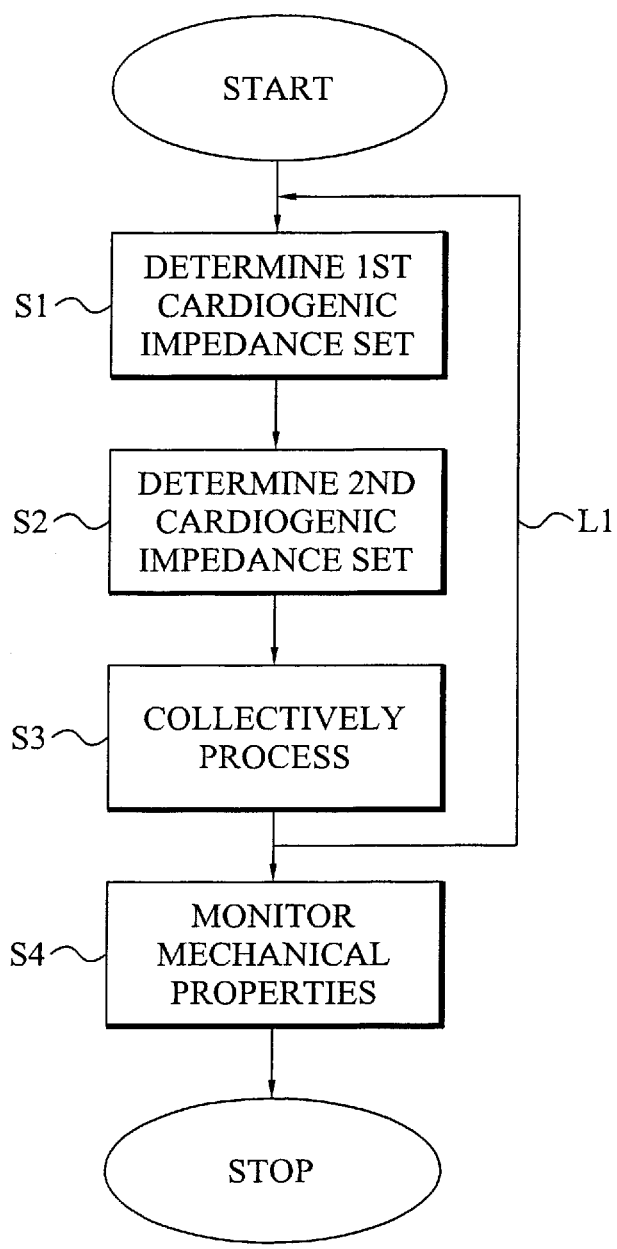
FIG. 1 is a flow diagram illustrating a method of monitoring mechanical heart properties according to the present invention.

Throughout the drawings, the same reference characters will be used for corresponding or similar elements.

The present invention generally relates to methods, devices and systems for monitoring the mechanical properties of the heart in a subject, preferably a mammalian subject and more preferably a human subject. These mechanical properties include the function of the heart in pumping blood through the pulmonary circuit/system and the systemic circuit/system.

By monitoring the mechanical heart properties it is possible to detect, even at an early instant, a change in the properties caused by different conditions directly effecting or indirectly effecting the subject's heart. For example, cardiac ischemia and other ischemic heart diseases, including heart infarcts, will cause stiffness to at least a portion of the heart muscle. This in turn affects the pumping function and thereby the mechanical properties of the heart. Other deleterious conditions affecting these mechanical properties include other forms of heart failure leading to increased heart size (hypertrophy) and poor inter-chamber synchronization causing tissue remodulation.

The monitoring of the present invention is based on measurement and processing of the cardiogenic impedance. As is used herein, cardiogenic impedance refers to impedance signals originating from the heart. The cardiogenic impedance is an impedance signal, preferably recorded inside the body of a subject, filtered to enhance the frequencies originating from the heart's mechanical activity.

Impedance recorded inside the body will consist of several different parts. There is one part originating from the (rather) constant amount of tissue between and in the vicinity of the electrodes used for measuring the impedance. This is a very slowly shifting part of the signal and is affected by, among others, the body composition. The lungs take up a large part of the thorax and each respiratory cycle affects the impedance as well. This is in part due to the fact that the increased amount of air in the thorax decreases conductivity, but also because of mechanical effects, e.g. tilting other organs, fat deposits, etc. altering what the measured impedance "sees". There is also a faster shifting part originating from the activity of the heart. If the impedance vector is inside or across the heart, the signal is composed in part of the shifting amount of blood the impedance vector sees and in part due to mechanical deformation. This does not necessary require that the actual heart is spanned by the impedance vector. In fact, the same kind of variations is obtained if the impedance is measured in the leg.

It has been discovered that the morphology of hear, as determined by the cardiogenic impedance, changes depending upon where a heart beat is occurring in the respiratory cycle. This respiratory cycle comprises a user inhalation and the following user exhalation or a user exhalation and the following inhalation, depending on where the start point of the respiratory cycle is defined. These morphological differences are not simple amplitude differences but have other fundamental origins. Without being bound by theory, a very fast regulatory system may be present that adapts the contraction pattern or stroke volume of the heart depending on the breathing, as signaled by, for example, oxygen saturation ($SO_2$) in the blood of the pulmonary vein. This regulatory system would then operate on a beat-to-beat basis. Alternatively, or in addition, the lungs mechanically influence the heart. Thus, during inhalation the lung volume increases and the lungs take up more space in the thorax, slightly altering the heart's geometry, e.g. by tilting and compressing the heart slightly. It is proposed that both these respiratory-originating effects will be a cause of the morphological differences.

These inter-beat variations in the cardiogenic impedance significantly change with a change in the mechanical properties of the heart. Thus, the difference in cardiogenic impedance in connection with maximum lung volume (filled lungs) and minimum lung volume (empty lungs) will change as the mechanical properties or the heart change, as illustrated by exposing the heart to certain provocations or a deleterious heart condition.

In the prior art, the respiratory dependence of the cardiogenic signal is most often, more or less effectively, filtered away. In clear contrast, the present invention acknowledges it and uses the information hidden in the respiratory effect on the cardiogenic impedance.

FIG. 1 is a flow diagram illustrating a method of monitoring mechanical properties of a heart in a subject according to an embodiment of the present invention. The method starts in step S1, where a first set of multiple cardiogenic impedance values are determined. These impedance values are reflective of the impedance of the heart in connection with a transition from inhalation to exhalation in the subject. Thus, these impedance values reflect the cardiogenic impedance at or close to maximum lung volume. A next step S2 determines a corresponding second set of multiple cardiogenic impedance values. These values are reflective of the cardiogenic impedance in connection with a transition from exhalation to inhalation in the subject. This means that the values reflect the cardiac impedance at or close to minimum lung volume.

The impedance values of the first and second set are collectively processed in a next step S3. This collectively processing involves determining or estimating a trend parameter based on the cardiogenic impedance values determined in steps S1 and S2. This trend parameter is indicative of the morphological difference in the cardiogenic impedance signal in connection with inhalation-exhalation transition as compared to exhalation-inhalation transition.

The determining steps S1 and S2 and the collectively processing step S3 is repeated multiple times as schematically illustrated by the line L1. This means that a plurality of trend parameters will be determined, where each such trend parameter is generated from the cardiogenic impedance values of a respective pair of first and second value sets. As these trend parameters reflect the morphological cardiogenic impedance difference over time, they are used in a next step S4 to monitor the mechanical properties of the heart. Thus, the trend parameters obtained by repeating the loop of steps S1 to S3, or at least a portion thereof, are processed in step S4 for proving this property monitoring.

It is possible to use different time frames when repeating the loop of steps S1 to S3. For example, these steps S1 to S3 could be conducted several times during a day and night, such as every few hours. Changes in the mechanical properties occurring during that day can then be early detected. However, for most practical implementation it might be enough to collect trend parameters once per day, every second day, every third or even more seldom.

In further embodiment, multiple trend parameters can be generated per day and the average of these parameters are calculated and stored for usage in the monitoring. In such a case, only one trend parameter need to be stored per measuring day, but this value will be an average of multiple values collected during different time instances that day. This will level out any background noise due to different subject postures, physical activity and other factors that could have an effect on the measurements. The monitoring of step S4 will then be conducted based of multiple average trend parameters, each being averaged over one day, a part of a day or a longer period than a day.

In the case of a change in the mechanical properties of the heart, such as an ischemic condition, this change will be reflected in the values of the trend parameters. This means that the processed trend parameters can be employed as decision support information for deciding whether a deleterious heart condition is present and whether any actions should be taken.

The method then ends.

Figure 2:
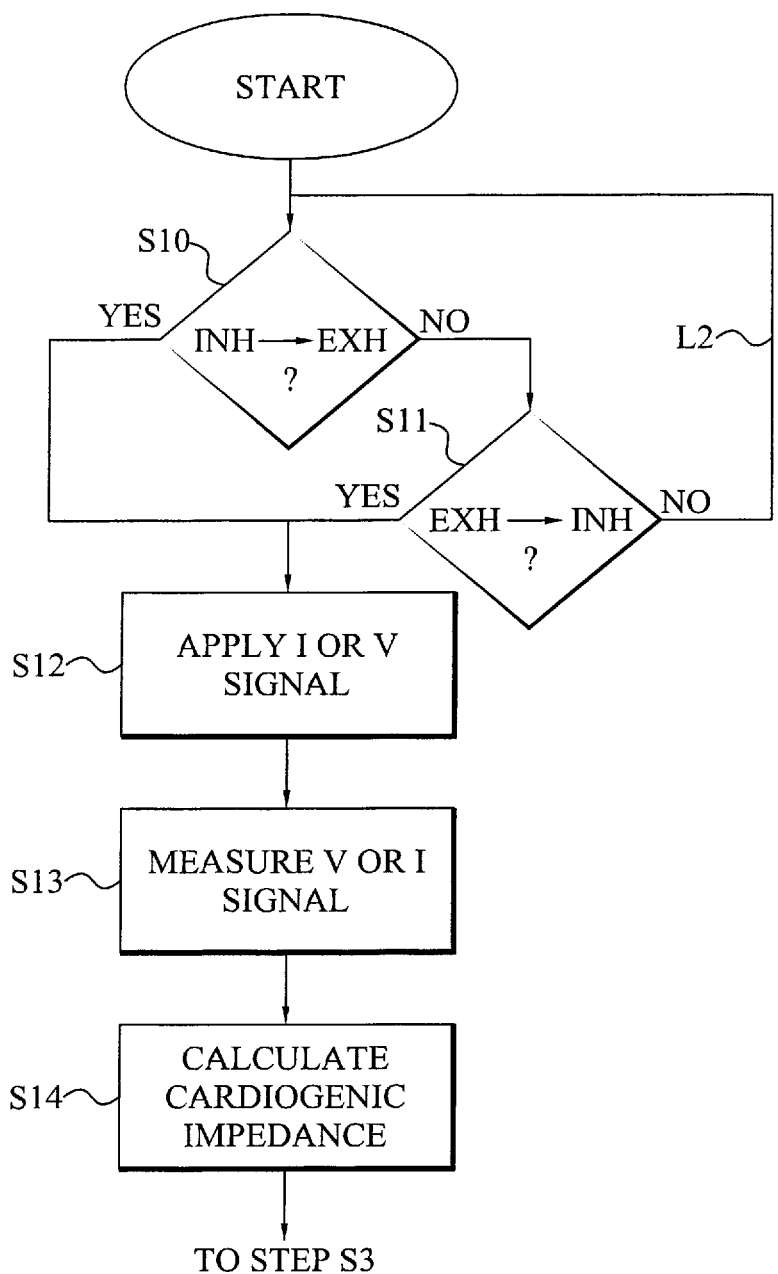
FIG. 2 is a flow diagram illustrating an embodiment of the determining steps of FIG. 1 in more detail.

FIG. 2 is a flow diagram illustrating an embodiment of the determining steps S1 and S2 of FIG. 1 in more detail. The method starts in step S10, where it is identified whether the subject has inhaled and is about to start exhaling, i.e. whether the subject is in the transition from inhalation to exhalation in the respiratory cycle. In such a case the method continues to step S12 where a current signal or a voltage signal is applied to subject. In a preferred embodiment, this current/voltage signal is applied using electrodes implanted in the thorax of the patient, such intra-thoracic, intra-cardiac and/or epi-cardiac electrodes. The usage and positioning of such implanted electrodes will be described in further details herein.

The applied current and voltage signal is preferably in the form of a train of current or voltage pulses. In the art of impedance measurement, different such pulse trains have been suggested. Any such prior art known pulse-based signal can be used in connection with the present invention. Thus there is a freedom in selecting particular pulse shape (amplitude(s), pulse form, current/voltage step or change, duration, etc.). In addition, the sampling rate, i.e. the time between applying these current or voltage pulses can also non-inventively be selected by the person skilled in the art. In order to provide a suitable amount of resulting voltage or current values a sampling rate of at least about 10 Hz is preferred, preferably at least about 50 Hz. An example of a current pulse tested with good result first applies a negative current pulse, directly followed by a positive current pulse and then ends with a second negative current pulse. The two negative current pulses preferably have same amplitude and duration. Examples of suitable current amplitudes include $-250$ µA, $-187.5$ µA, $-125$ µA and $-62.5$ µA. The positive pulse could, for example, have any of the following amplitudes 1000 µA, 750 µA, 500 µA, 250 µA. The current pulse width could be in the interval of 14 µs to 40 µs.

Possible sampling rates that could be used include, but are not limited to, 16 Hz, 32 Hz, 64 Hz and 128 Hz.

In a next step S13, a resulting voltage or current signal is measured using a pair of electrodes, preferably implanted electrodes in the subject. If a current signal, such as current pulse, was applied in step S12, the step S13 measures a resulting voltage signal and vice versa. The same electrodes used for applying the current/voltage signal can be used for measuring the resulting voltage/current signal, i.e. a bipolar electrode arrangement is employed. Alternatively, one of the electrodes could be common for the signal application and the signal measurement, i.e. a tripolar arrangement, or dedicated application and measurement electrodes could be employed, denoted quadropolar arrangement in the art.

Information of the applied current/voltage signal and the measured voltage/current signal is used in step S14 for calculating the cardiogenic impedance in connection with the inhalation-to-exhalation transition. The "area" of the current (voltage) pulse is known and the "area" of the sensed voltage (current) is computed. A cardiogenic impedance value is then calculated as the ratio between the voltage and the current.

As the applied signal is preferably in the form of multiple separate current or voltage pulses, multiple cardiogenic impedance values can be calculated in step S14 and constitute the first value set of the invention.

In a preferred implementation of the invention, the application of the current or voltage signal in step S12 is preferably performed during a heart cycle or cardiac cycle occurring in connection with the inhalation-to-exhalation transition. As is well-known in the art, a cardiac cycle involves the three major stages: atrial systole, ventricular systole and cardiac diastole. A cardiac cycle can, for instance, be defined as the period from one R-wave to the next, i.e. as so-called RR-interval. This should, however, merely be seen as an illustrative and non-limiting example of defining the start point and end point of a cardiac cycle.

In a more preferred implementation, the current or voltage signal is applied in step S12 in connection with a defined period of the cardiac cycle coincident with or being close, preferably closest, in time to the inhalation-to-exhalation transition. This defined period is preferably the period of the cardiac cycle where the cardiogenic impedance is largest, i.e. corresponds to peak in the impedance. This period generally corresponds to the interval from about 100 ms to about 400 ms following an R-wave. However, the actual position of the interval following an R-wave may differ slightly depending on subject age, sex, health condition, activity level, etc.

The method then continues to step S10 for also generating multiple cardiogenic impedance values for the second value set, which is schematically illustrated by the line L2.

If it is determined that the current state in the respiratory cycle is not an inhalation-to-exhalation transition the method continues from step S10 to step S11. In this step S11, it is identified whether the respiratory state is in the transition from exhalation to inhalation. If this is not the case, the method continues anew to step S10.

However, if the state is an exhalation-to-inhalation transition, the method continues to step S12, where a current or voltage signal is applied. The operation of this step S12 and the following steps S13 and S14 is conducted in the same manner as previously described. The cardiogenic impedance values calculated in step S14 are thus reflective of the cardiogenic impedance during the exhalation-to-inhalation transition, preferably during a cardiac cycle occurring in connection with (coincident with or being close to) the transition and more preferably during the defined period of that cardiac cycle. The resulting cardiogenic impedance values constitute the second value set of the invention.

The method then continues to step S3 of FIG. 1 where the calculated impedance values of the first and second sets are collectively processed to generate a trend parameter.

It is anticipated by the present invention that the order of steps S10 and S11 can be interchanged without affecting the result of the operation of the invention.

Figure 3:
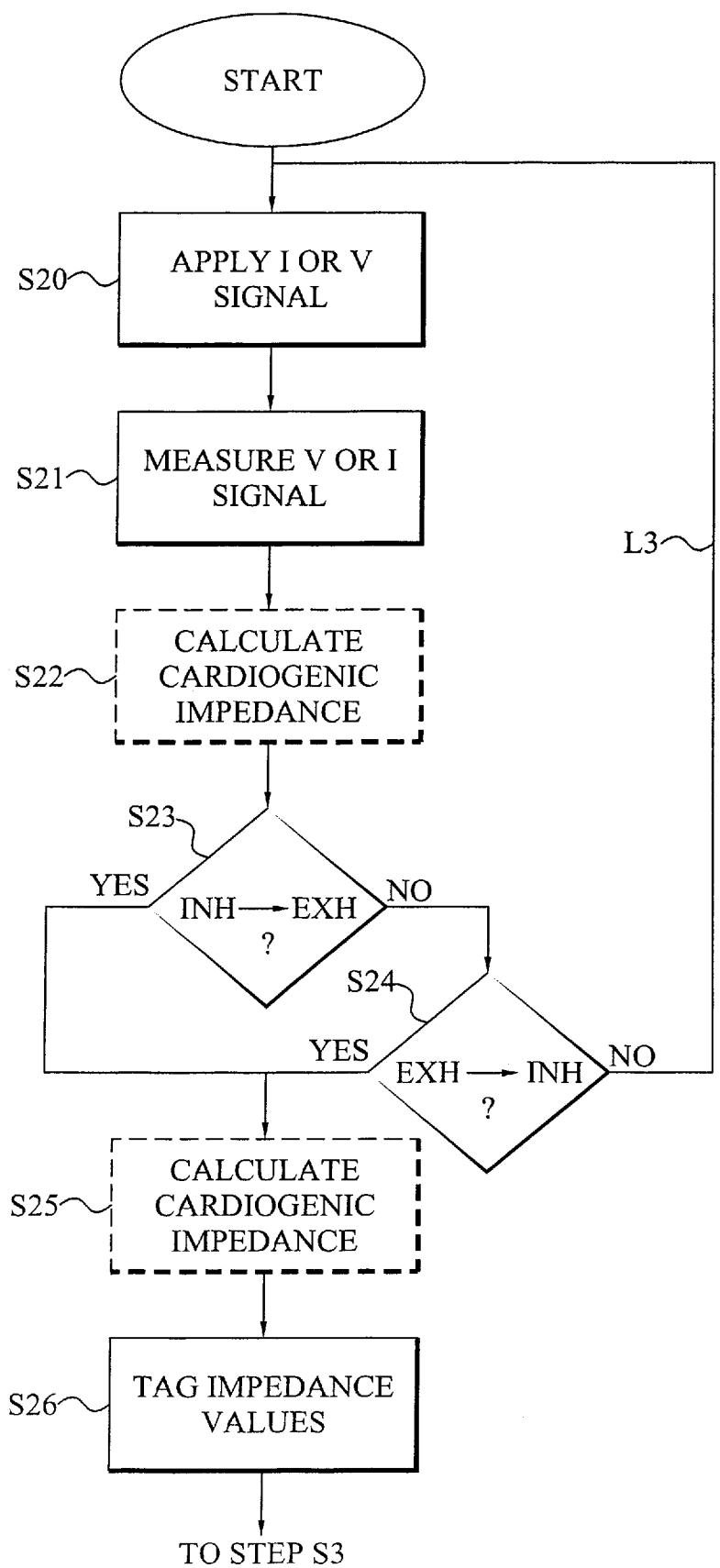
FIG. 3 is a flow diagram illustrating another embodiment of the determining steps of FIG. 1 in more detail.

FIG. 3 is a flow diagram illustrating another embodiment of the determining steps S1 and S2 of FIG. 1 in more detail. The method starts in step S20, where a current or voltage signal is applied to the subject. This step basically corresponds to step S12 of FIG. 2 and is not described further herein. The resulting voltage or current signals are measured in a next step S21, which is performed as previously described in connection with step S13 of FIG. 2.

In an optional step S22, information of the applied signal and the measured signal is employed for calculating cardiogenic impedance values. This is performed as described in connection with step S14 of FIG. 2. Thereafter it is determined whether the respiratory cycle state is in the transition from inhalation to exhalation in step S23 or in the transition from exhalation to inhalation in step S24. If respiratory state is neither of these transitions the method is returned to step S20, which is schematically illustrated by the line L3.

If, however, the state is one of the transitions, the method continues to step S25, where cardiogenic impedance values are calculated unless this was performed in step S22. The operations in this step S25 are similar to those in step S14 of FIG. 2. In either case, the cardiogenic impedance values occurring in connection with the inhalation-to-exhalation transition or the exhalation-to-inhalation transition, preferably occurring during a cardiac cycle occurring in connection with the transition and more preferably during the defined period of that cardiac cycle, are tagged in step S26. This value tagging identifies whether the cardiogenic impedance values belong to the first value set or the second value set of the invention.

Once cardiogenic values of both the first set and the second set have been calculated and tagged, the method continues to step S3 of FIG. 1, where a trend parameter is calculated from the values.

In contrast to FIG. 2, this embodiment involves continuously or periodically applying a current or voltage signal and measuring the resulting voltage or current signal during a measuring period. This means that several of the measured voltage/current values and calculated impedance values if step S22 is performed will not be used according to the invention. Only those voltage/current values and calculated impedance values measured in connection with the inhalation-to-exhalation and exhalation-to-inhalation transitions, more preferably such values registered through a cardiac cycle, or a defined portion of a cardiac cycle occurring in connection with the transitions, will be employed for the purpose of the invention.

Different techniques can be employed for determining where in the respiratory cycle, the cardiogenic impedance values should be collected to coincidence with or falling close to the transitions between inhalation and exhalation and vice versa. For example, external stretch sensors and gauges or pressure sensors could be connected to the chest of the patient for following the movement of the lungs. In a similar manner, implanted stretch or pressure sensors could alternatively be used for synchronizing the cardiogenic impedance measurement or tagging with the correct intervals (transitions) in the respiratory cycle. A further possible technique could be the recording of intra-cardiac electrograms (IEGMs). The respiratory signal can be identified by low-pass filtering the IEGM signal, e.g. by using a cut-off frequency of about 0.2-0.5 Hz. Still another possibility is to use the measuring technique described above in connection with FIG. 3, in other words, more or less continuously or periodically measure the cardiogenic impedance during measurement intervals. A copy of this impedance signal can then be low-pass filtered in similarity to the IEGM signal (cut-off frequency of about 0.2-0.5 Hz) to follow the respiratory signal.

Figure 4:
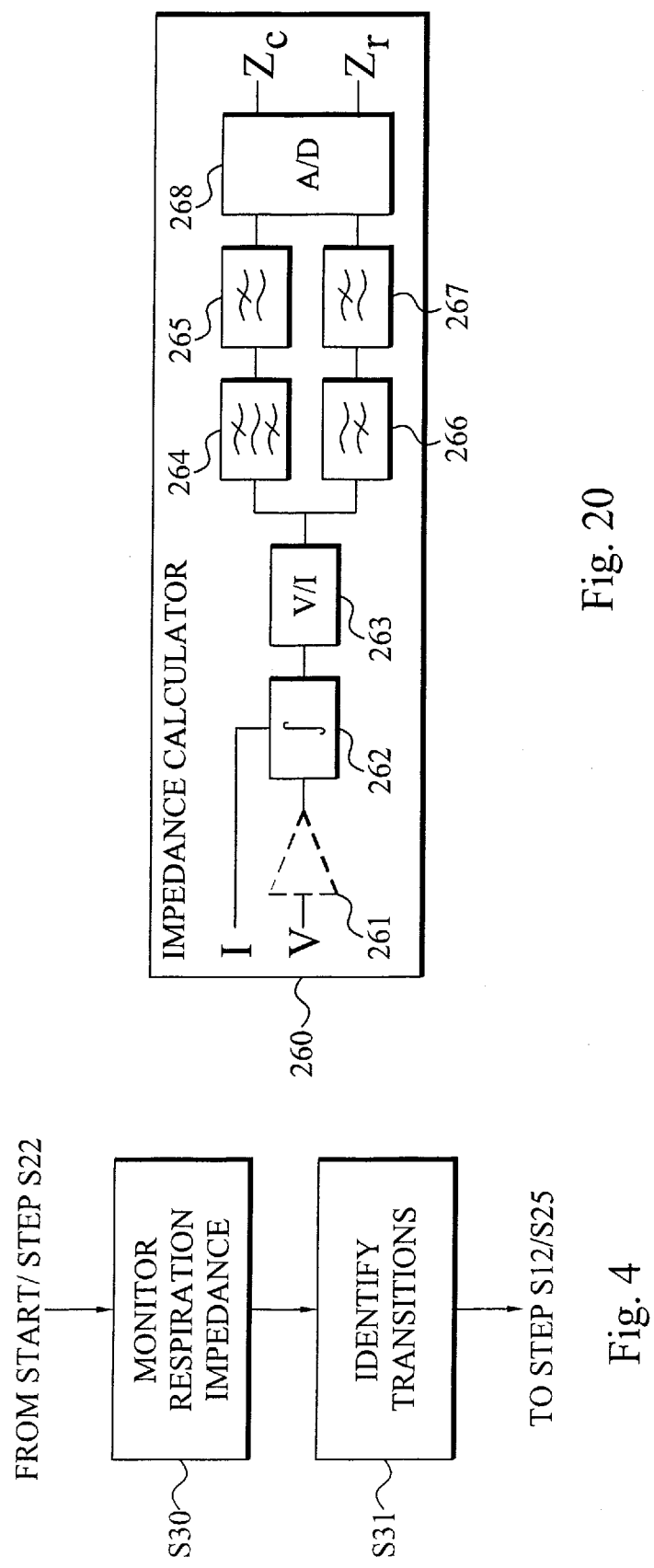
FIG. 4 is a flow diagram illustrating an embodiment of the detecting steps of FIG. 2 or FIG. 3 in more detail.

FIG. 4 is a flow diagram illustrating a further possibility of identifying the inhalation-to-exhalation and exhalation-to-inhalation transitions in the respiratory cycle. The method continues from start in FIG. 2 or step S22 in FIG. 3. In a next step S30, a respiratory impedance signal comprising multiple respiratory impedance values is generated. This respiratory or respiration impedance can be used as an indication of or for following respiratory volume changes. The respiratory impedance is accomplished by the passing of a very small electrical current (or voltage) across the subject's chest electrodes and measuring the change in impedance as the chest volume changes. The impedance is a result of air (which is a poor electrical conductor), moving into the lungs and thereby changing the volume of the lungs. It is often possible to obtain this respiratory impedance signal from the same applied current/voltage signal and the resulting measured voltage/current signal as was used for generating the cardiogenic impedance signal. This possible by applying different filtering to the raw impedance signal to get both the cardiogenic impedance signal and the respiratory impedance signal. In a preferred implementation, the respiratory impedance of the invention is respiratory AC impedance.

Figure 6:
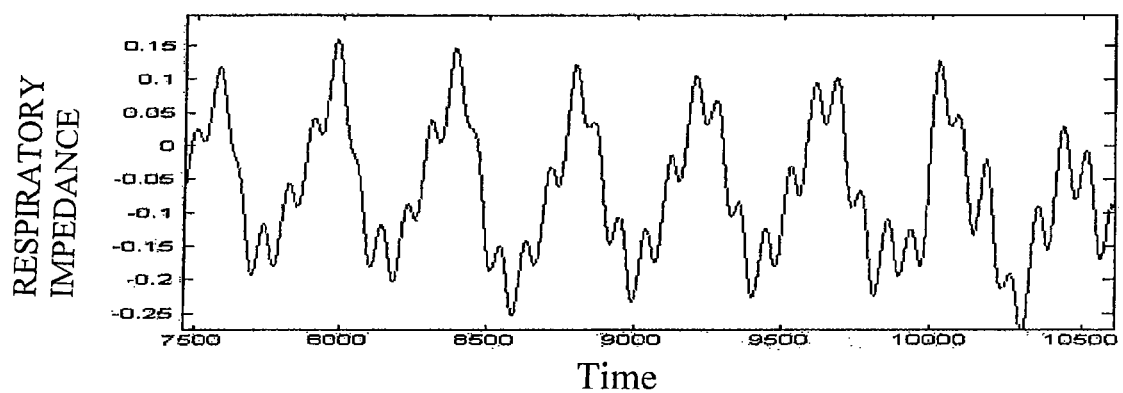
FIG. 6 is a diagram illustrating results of respiratory impedance measurements according to the present invention.

FIG. 6 is a diagram of the respiratory signal from a bipolar recording from the ring electrode of a right ventricular (RV) lead to the can. The respiratory cycle is clearly evident from such a recording. The respiratory impedance increases during inhalation up to the peak (local maximum) corresponding to the transition from inhalation to exhalation. At this peak, the volume of the lungs is at maximum during the cycle. As the subject exhales the respiratory impedance drops down to a local minimum or minimum plateau. At this minimum the transition from exhalation to inhalation is taking place. This corresponds to minimum lung volume during the cycle.

In FIG. 4, the recorded respiratory impedance signal is monitored in step S30 to identify, in step S31, the transitions taking place in the respiratory cycle. In other words, this identifying step S31 identifies the maximum and minimum points or plateaus in the respiratory cycle. The cardiogenic impedance values of the invention are then collected or tagged in connection with the maximum and minimum values/plateaus in step S12 of FIG. 2 or step S25 of FIG. 3.

In a typical implementation, the cardiogenic cycles coinciding with or being closest in time to the maximum or minimum value of the respiratory impedance during a respiratory signal are identified. The cardiogenic impedance values are then generated or tagged during these identified cardiogenic cycles or more preferably during defined periods of the identified cycles.

It is anticipated by the present invention that for most practical implementation it is not absolutely necessary to employ cardiogenic impedance values occurring during the heart cycle being closest in time to the peaks and valleys in the respiratory impedance signal. For example, a first cardiogenic cycle might occur shortly before a peak in the respiratory signal with a second cardiogenic cycle occurring shortly after the peak. This second cycle could be closer in time to the peak top as compared to the first cycle. However, the monitoring of the mechanical properties of the invention may indeed be successfully performed even when employing the first cardiogenic cycle over the second cycle. Thus, it is necessary that the cardiogenic impedance values of the invention are collected in connection with the respiratory transitions (maximums and minimums) but they must not necessarily coincident with the transitions. It may actually more advantageous for some heart conditions to select cardiogenic cycles not being closest in time to the peaks and values, such as the first cycle above. For example, the cardiogenic impedance values recorded during at least a portion of the cardiogenic cycle occurring closest to the maximum/minimum values in FIG. 6 but on a defined position relative the maximum/minimum values. Thus, impedance values collected close to the end of the inhalation stage (or at the beginning of the exhalation stage) of the respiratory cycle could be used as impedance values occurring in connection to the inhalation-to-exhalation transition. Correspondingly, impedance values collected close to the end of the exhalation stage (or at the beginning of the inhalation stage) are used as such values occurring in connection with the exhalation-to-inhalation transition.

Depending on how the subject is actually inhaling and exhaling, the peaks and/or valleys in FIG. 6 could instead be maximum or minimum plateaus. In such a case, it could be possible that at least two cardiogenic cycles take place during such a plateau in the respiratory signal. The cardiogenic impedance values recording at a period of any of these at least two cardiogenic cycles could then be employed according to the invention.

Figure 5:
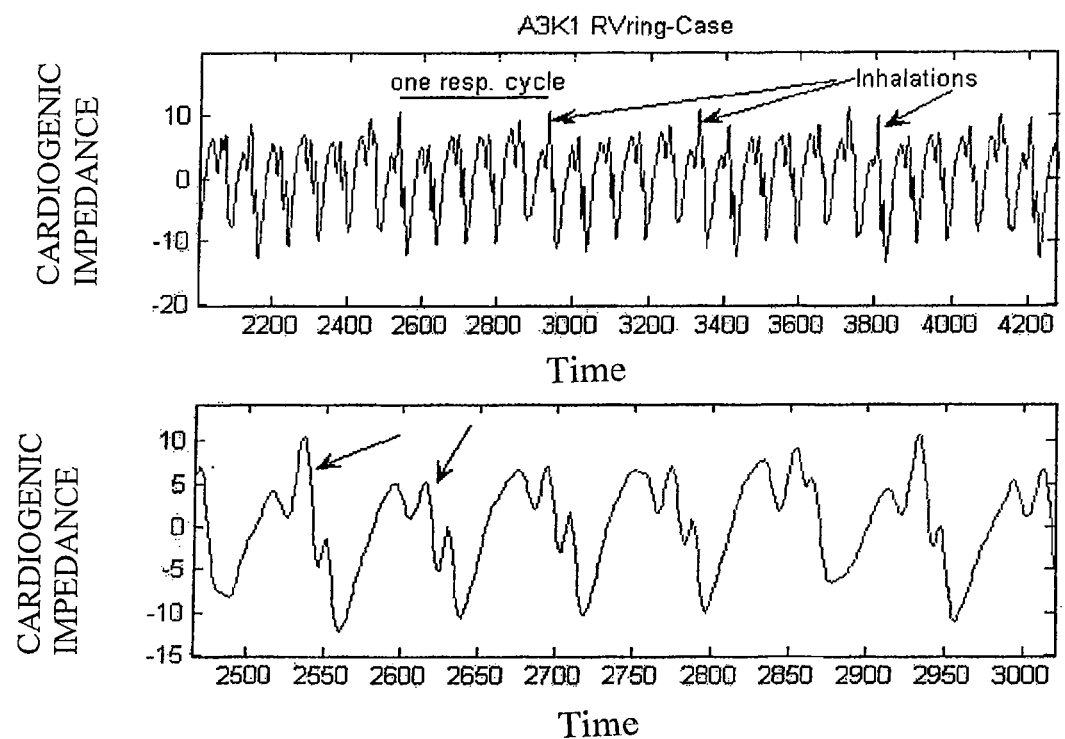
FIG. 5 is a diagram illustrating results of cardiogenic impedance measurements according to the present invention.

FIG. 5 is a diagram illustrating the cardiogenic impedance signal recorded as taught by FIG. 3, i.e. more or less continuously during a time interval. In this case, bipolar measurements between RV ring electrode and can electrode have been used to generate the cardiogenic impedance signal. In the upper plot, the respiratory cycles are evident, slowly modulating the signal. The lower plot is a magnification of the impedance signal during the respiratory cycle marked in the upper plot. In this plot it is clearly shown that the cardiogenic content of the impedance signal changes depending on where we are in the respiratory cycle.

As was described in the foregoing, the cardiogenic impedance values are preferably determined for a defined period of a cardiac cycle, where the defined period corresponds to the peak of the impedance signal. In the lower plot several such cardiac cycles are illustrated. The defined period corresponds to the peak of the cardiogenic impedance. For example, if the cardiogenic cycle corresponding to sample 2725 to 2800 coincidences with the exhalation-to-inhalation transition, the impedance values corresponding to sample 2737.5 to 2780 could be useful in the monitoring of the invention.

Figure 7:
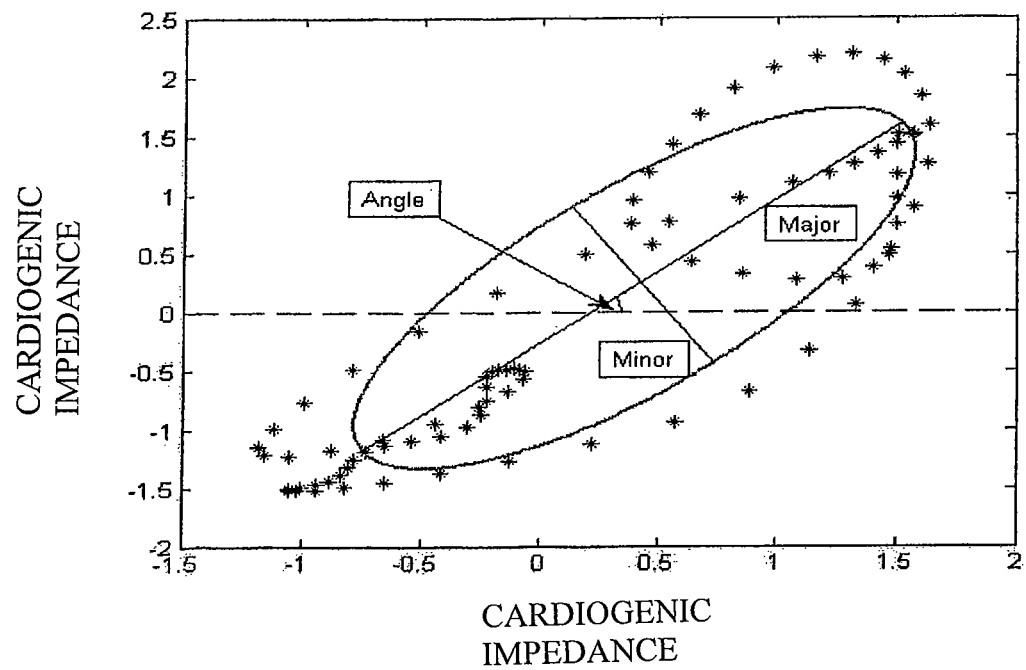
FIG. 7 is a diagram illustrating fitting an ellipse to cardiogenic impedance values according to the present invention.
Figure 8:
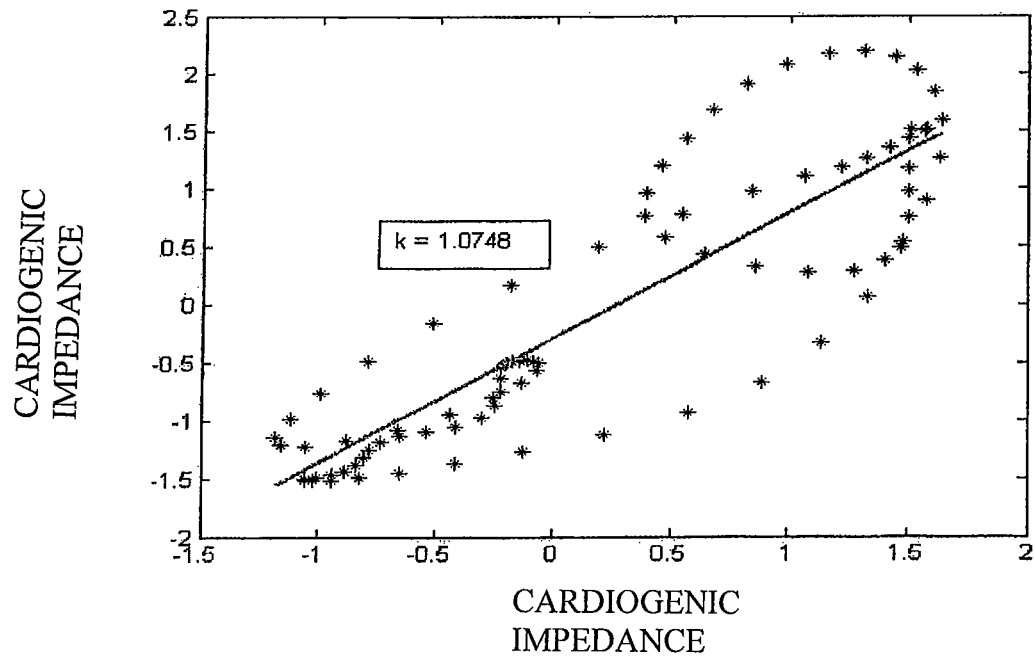
FIG. 8 is a diagram illustrating fitting a straight line to cardiogenic impedance values according to the present invention.

The collectively processing of the cardiogenic impedance values of the two value sets collected during a same respiratory cycle can be performed in vastly different manners. In a preferred approach, the impedance values of the second value set (or first value set) are regarded as functions of the impedance values of the first value set (or second value set). The impedance values could then be plotted with the second set values on the y-axis and the first set values on the x-axis. If the two sets do not contain the same number of impedance values, spline interpolation can be employed to form equally large sets. FIGS. 7 and 8 are two diagrams illustrating such a value plotting. It is clear from these diagrams that the cardiogenic impedance is different depending on where it is measured in the respiratory cycle, otherwise all plotted points would lie on a straight line with slope k=1.

The trend parameter is obtained by processing the plot points depicted as "*" in the diagrams. The trend parameter of the invention is a quantity reflecting the respiratory difference in the cardiogenic impedance. Starting from the collected impedance values and generating the plot points as illustrated in FIGS. 7 and 8, different parameters reflecting the difference in the cardiogenic impedance values can be determined.

FIG. 7 illustrates a first possible approach. In this approach an ellipse is fit to the plot points. This ellipse is preferable the ellipse that fit best to the points in sense of minimizing the mean square error (MSE) or some other error estimate. The trend parameter is then a parameter representative of the fitted ellipse. For example, the major axis of the ellipse illustrated in FIG. 7 can be used as a trend parameter of the invention. In addition, or alternatively, the angle between the major axis and the x-axis (also illustrated in FIG. 7) could be used as a trend parameter.

In a different approach, a straight line is fitted to the plot points as is shown in FIG. 8. This line is preferably the line that minimizes the MSE and can therefore be regarded as the straight line that best fits to the points. The trend parameter is then a parameter representative of the straight line, such as the slope of the line. Another example is to use the mean value of the squared difference between an estimated plot value and a true plot value as trend parameter. Thus, for each impedance value, x, of the first set, the corresponding "true" impedance value of the second set, $y_T$, and estimated value, $y_E$, as determined from the straight line are identified. The trend parameter T is then calculated as:

$$T = \frac{\sum_{i=1}^{N}(y_T^i - y_E^i)^2}{N}$$

where N is the number of values of the first (and second) value set. Instead of using the mean squared error as trend parameter, the correlation coefficient is computed from the covariance matrix. This correlation coefficient is then employed as trend parameter.

Figure 9:
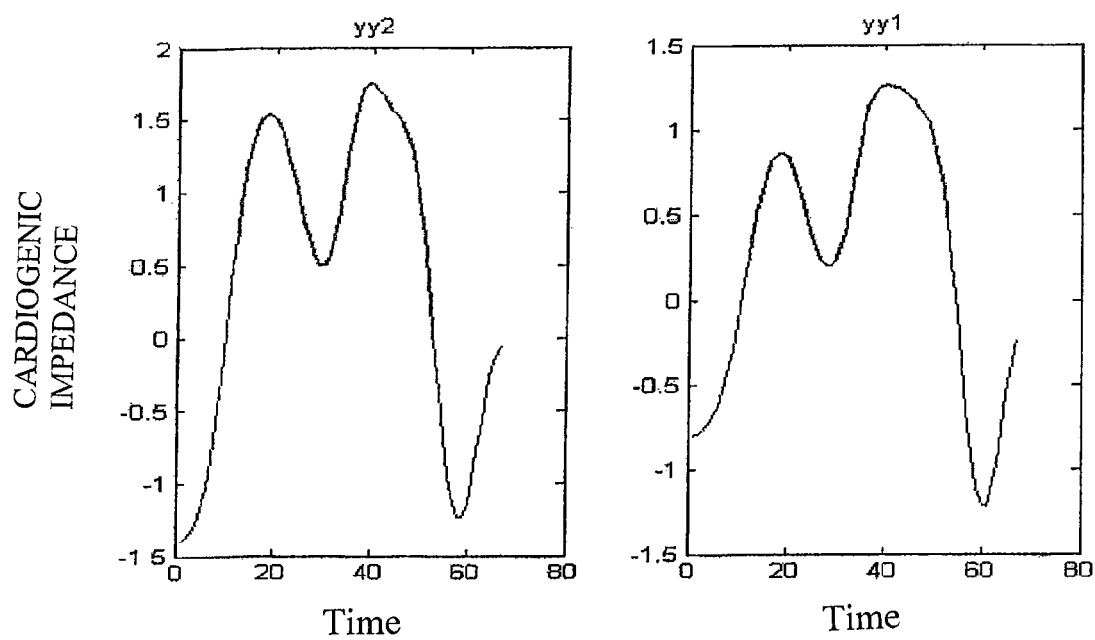
FIG. 9 is a diagram illustrating cardiogenic impedance values collected according to the present invention.

A slightly different approach is illustrated in FIG. 9. The two diagrams illustrate the different impedance values registered in connection with a cardiogenic cycle occurring in connection with inhalation-to-exhalation transition and exhalation-to-inhalation transition. In the figure, yy2 denotes the impedance values of the second set and yy1 denotes the values of the first set. The peak section of the two data sets, marked as a bold line in the figure, is identified. For each such top section, the variance among the selected samples is computed, resulting in two variance numbers. The trend parameter can then be calculated from these two variance numbers, such as the ratio between them.

The above given examples of calculated trend parameters should merely be seen as illustrative approaches of trend parameters that can be used according to the invention. Actually any parameter that is descriptive of the difference in cardiogenic impedance at the two measuring occasions (transitions) of a respiratory cycle can be used as trend parameter of the invention.

The trend parameter could also be a combination of two or more parameters. For instance, multiplying the ellipse major axis with the ellipse angle (in radians), gives a number that can be used as trend parameter.

In the monitoring of the mechanical properties of the heart, multiple trend parameters calculated as previously described and representative of different measuring periods are processed. In such a case, the trend parameters are preferably of a same type. Thus, they could all represent ellipse major axis or some other of the previously mentioned parameter types. The trend parameters can then be plotted over time to display any change in the mechanical properties of the heart.

Figure 10:
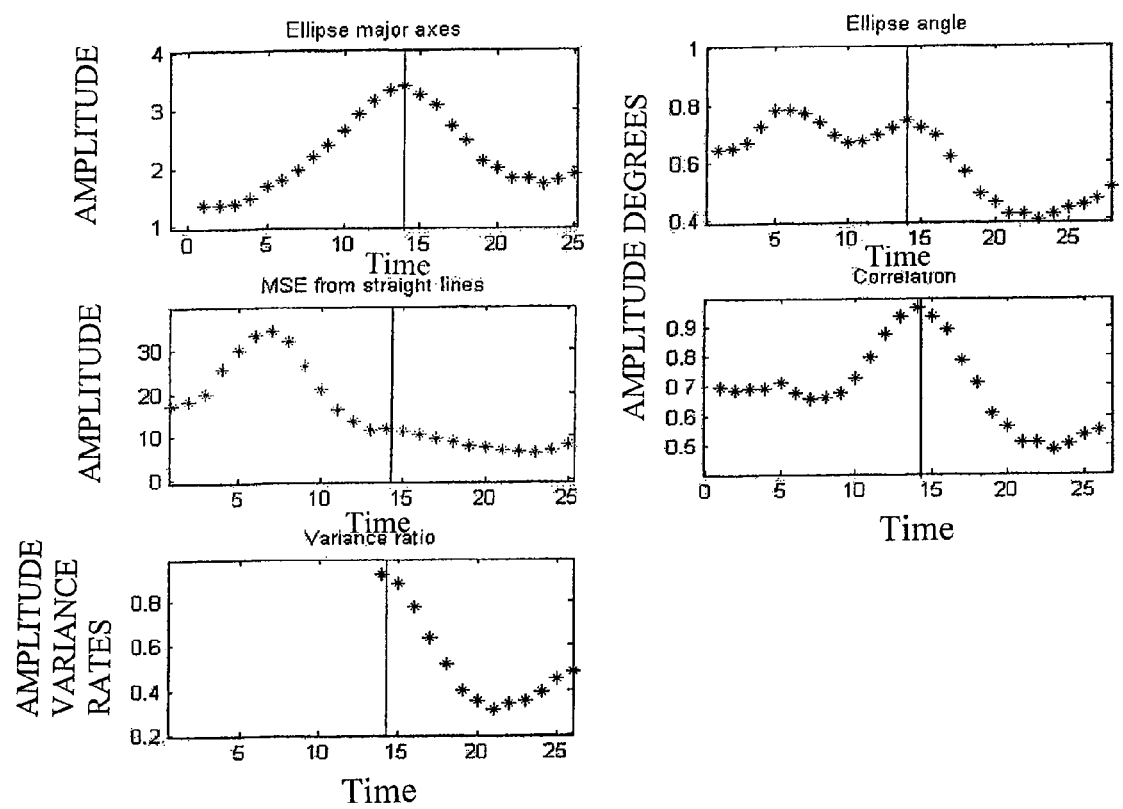
FIG. 10 illustrates diagrams of different trend parameters useful in monitoring mechanical heart properties of the present invention.

FIG. 10 is a diagram illustrating different such trend parameters over time. The diagrams are the result of ischemic experiments, where ischemia is induced in adult porcine through injection of micro spheres (sephadex provocation) in the left anterior descending coronary artery on the left side of the heart. This causes blocking of the coronary capillaries, causing a rather global ischemia. The onset of the micro sphere provocation is almost immediate and the vertical lines denote maximum provocation effect (with respect to change in contractility, cardiac output, stress, etc.). The following period corresponds to the recovery part. For the variance ratio, no impedance values were recorded during the provocation but merely in the recovery part.

Figure 11:
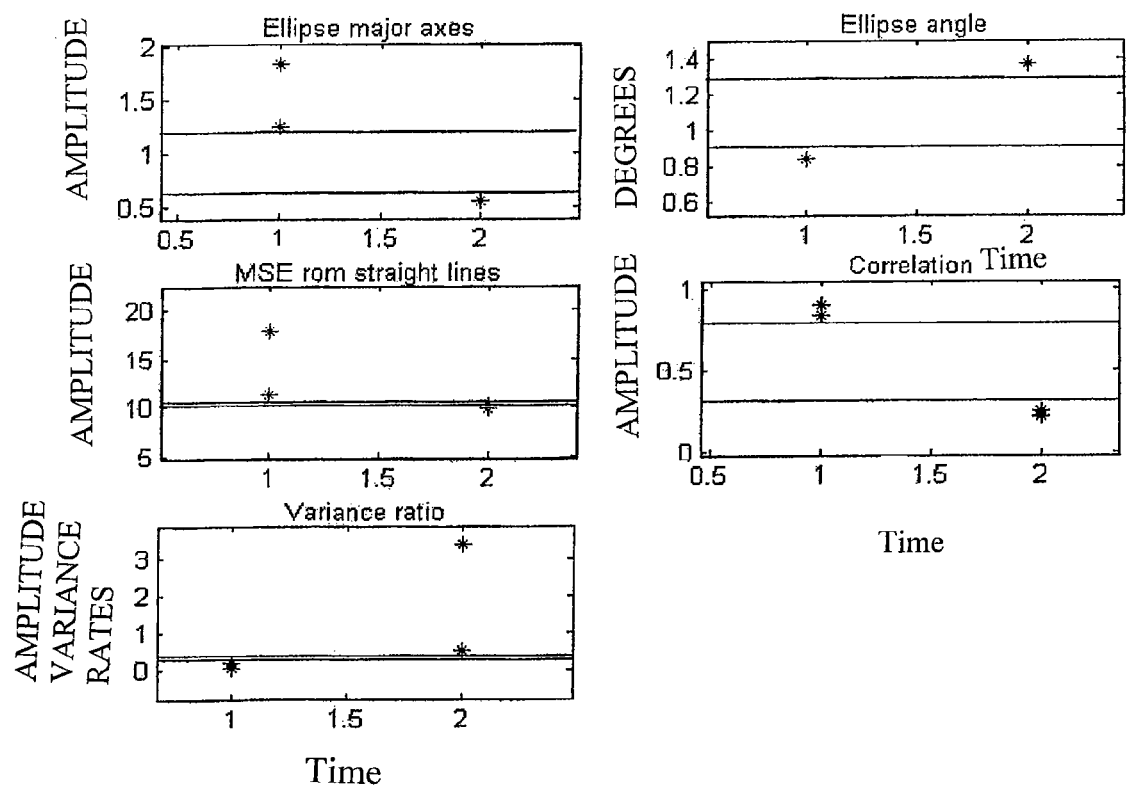
FIG. 11 illustrates diagrams of the trend parameters in FIG. 10 before and after an induced chronic hear failure.

FIG. 11 illustrates diagrams from experiments on a chronic heart failure (CHF) model on canine. This heart failure is induced through rapid pacing for several weeks. In these experiments, no posture knowledge was available as the animals were awake and free to move during the trails. In each diagram, two trend parameters from different times in healthy animal (at x=1) and two trend parameters from the same animal after heart failure was confirmed (x=2) are illustrated. From these diagrams it is clear that usage of ellipse major axis, ellipse angle or correlation parameter as trend parameter provides a good discrimination between healthy heart tissue and CHF.

Figure 12:
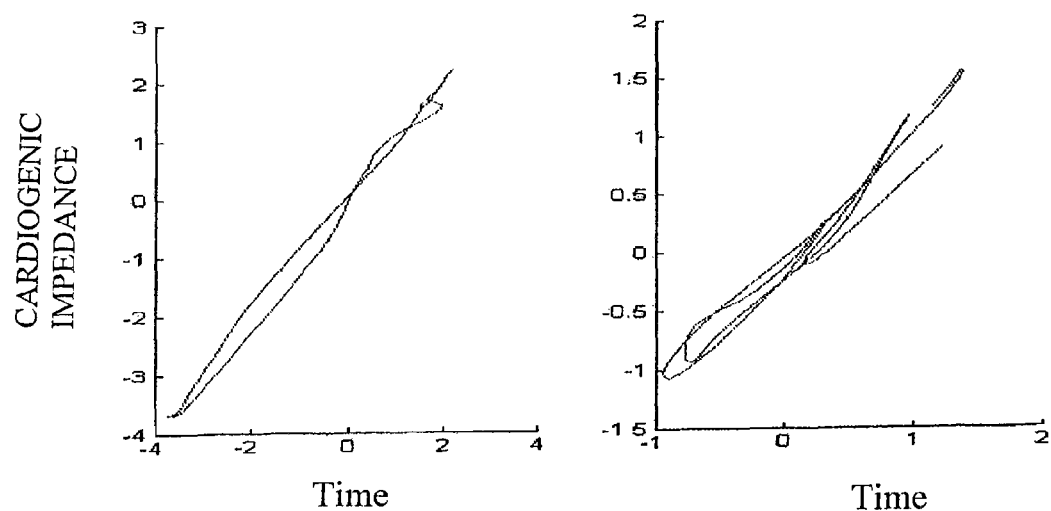
FIG. 12 illustrates diagrams displaying cardiogenic impedance values before (left) and after (right) induced heart ischemia.
Figure 13:
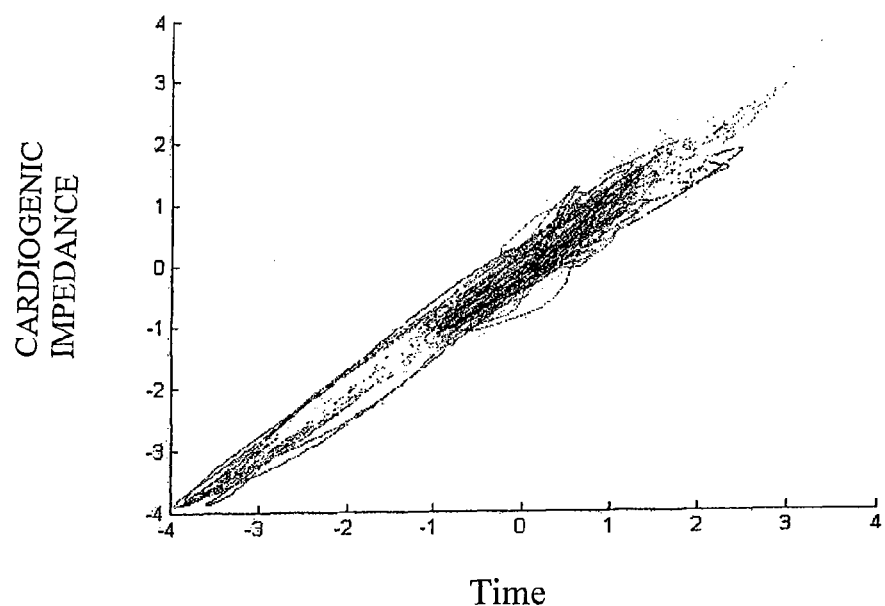
FIG. 13 is a diagram illustrating multiple loops of FIG. 12 before and after induced heart ischemia.

FIG. 12 illustrates a loop of a cardiogenic impedance values during a respiratory cycle, where the values of the second value set have been plotted as functions of the impedance values of the first set. The leftmost plot corresponds to healthy heart tissue, whereas the rightmost plot is after sephadex provocation, i.e. after cardiogenic ischemia. In clear contrast to the diagrams of FIGS. 7 and 8, the plot points are now interconnected to form the illustrated loops. FIG. 13 illustrates several overlaid loops of FIG. 12 over time. In this diagram, the light gray loops are the results before provocation and the dark loops are after provocation. It is clear from this figure that there is difference in impedance values before and after provocation as the loops after ischemia have markedly different shape as compared to the pre-ischemia loops.

Figure 14:
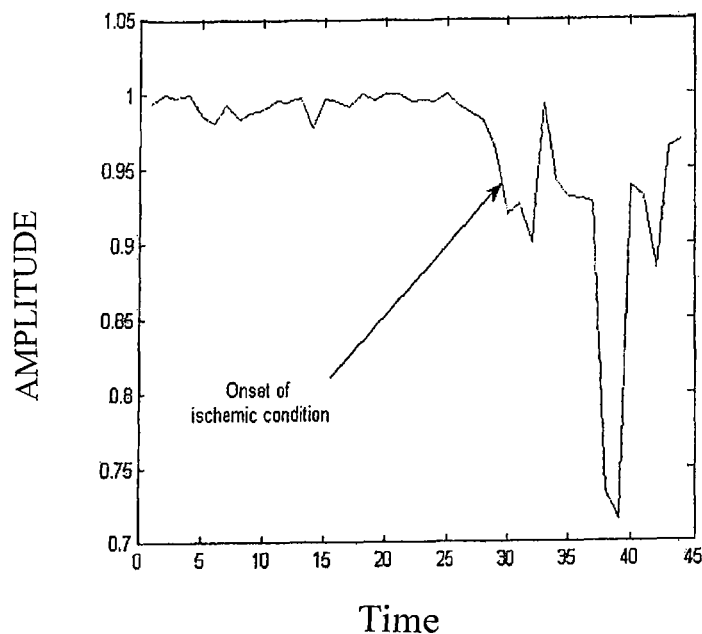
FIG. 14 is a diagram illustrating monitoring of a trend parameter determined from the diagram of FIG. 13.
Figure 15:
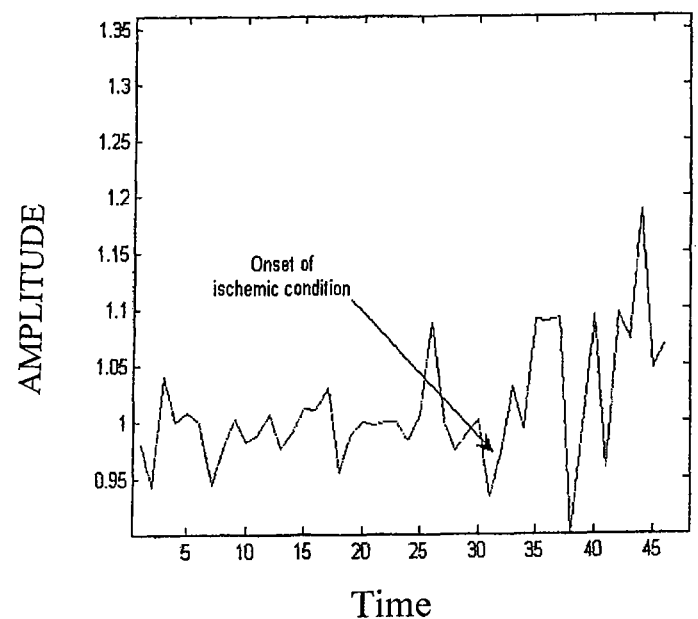
FIG. 15 is a diagram illustrating monitoring of another trend parameter determined from the diagram of FIG. 13.

FIGS. 14 and 15 are diagrams over trend parameters from impedance values recorded before and during the onset of ischemic condition. In FIG. 14, the trend parameter is in the form of the slope of a line fitted to plot points (loop) and in FIG. 15, the correlation coefficient is used as trend parameter. There is a clear reduction in the slope following ischemia in FIG. 14, whereas the variance of the correlation increases after ischemia in FIG. 15.

The methods according to the present invention may be implemented as software, hardware, or a combination thereof. A computer program product implementing the methods or a part thereof comprises software or a computer program run on a general purpose or specially adapted computer, processor or microprocessor. The software includes computer program code elements or software code portions that make the computer perform the methods using at least one of the steps previously described in FIGS. 1 to 4. The program may be stored in whole or part, on, or in, one or more suitable computer readable media or data storage means such as a magnetic disk, CD-ROM or DVD disk, USB memory, hard disk, magneto-optical memory storage means, in RAM or volatile memory, in ROM or flash memory, as firmware, or on a data server.

Figure 16:
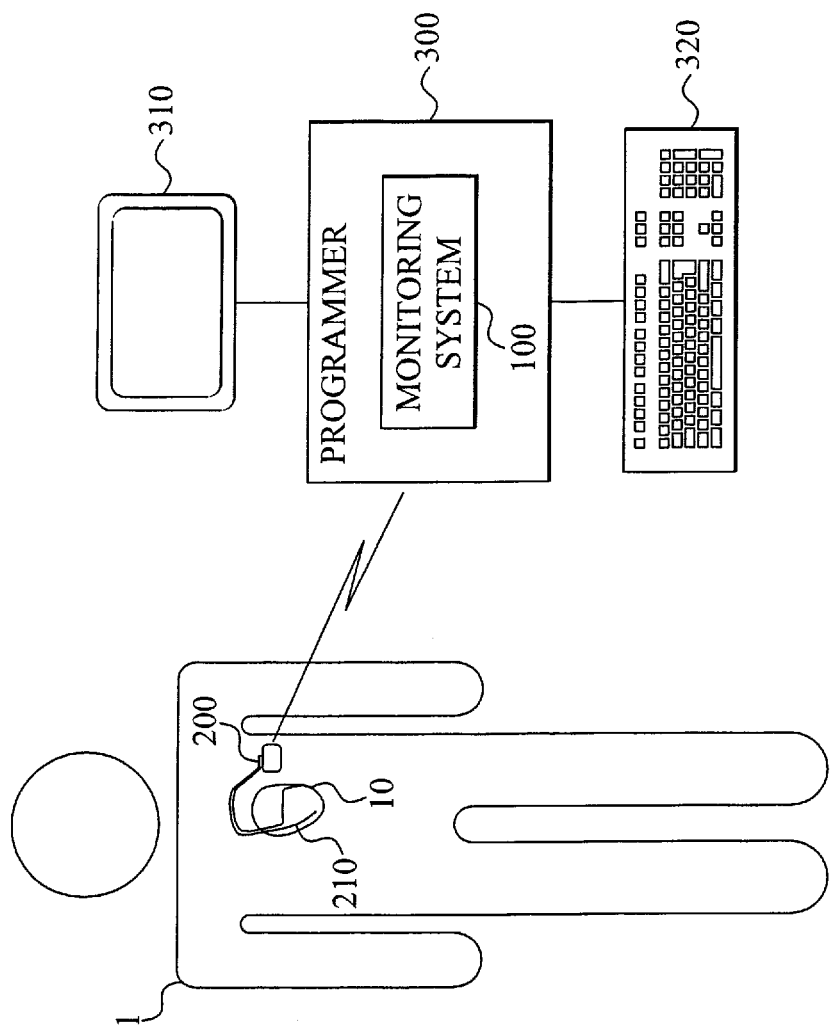
FIG. 16 schematically illustrates a patient equipped with an implantable medical device according to the invention and the communication between the implantable medical device and an external programmer.

FIG. 16 is a schematic overview of a subject 1 equipped with an implantable medical device (IMD) 200 connected to the subject's heart 10. The IMD 200 is illustrated as a device that monitors and/or provides therapy to the heart 10 of the patient 20, such as a pacemaker, defibrillator or cardioverter. However, the present invention is not limited to cardiac-associated IMDs but may also be practiced with other implantable medical devices, such as drug pumps, neurological stimulators, physical signal recorders, oxygen sensors, or the like, as long as the IMD 200 is equipped with or is connected with equipment 210 allowing measurement of the cardiogenic impedance of the subject's 1 heart 10.

In the figure, the IMD 200 is connected to two leads 210 inserted into the heart 210 and the right and left ventricle. These leads 210 are equipped with electrodes, such as tip electrodes, ring electrodes and/or coil electrodes, depending on what impedance vector is desired. The IMD 200 must not necessarily have two different leads but could instead use a single lead. Depending on the number of leads 210 and their intra-cardiac position, different impedance vectors are possible and within the scope of the invention. For example, the impedance vector could be between right ventricle (RV) and right atrium (RA), left ventricle (LV) and left atrium (LA), RV and LA, LV and RA, RV and LV and RA and LA. Furthermore, epicardiac and intra-thoracic electrodes could also be employed, e.g. using the IMD body or can 200 as one electrode.

Bipolar, tripolar or quadopolar measurements are possible and within the scope of the invention. Generally, better result is obtained if the electrodes are not positioned too close.

As will be described in more detail herein, the monitoring system of the invention or at least a portion therefore can be implemented in the IMD 200. In an alternative approach, the monitoring system 100 or at least a portion therefore is implemented in an external device 300. This external device 300 could be a programmer as illustrated in the figure, a physician's workstation, a home monitoring device or actually any data processing unit having capability of receiving data collected by the IMD 200. The external device 300 could receive this data through direct communication with the IMD 200 or via an intermediate communications module/unit operating as a relay device.

The external device 300 is preferably connected to a display screen 310 allowing display of the calculated trend parameters of the invention for allowing the subject 1 or a physician to monitor the trend parameters.

Figure 17:
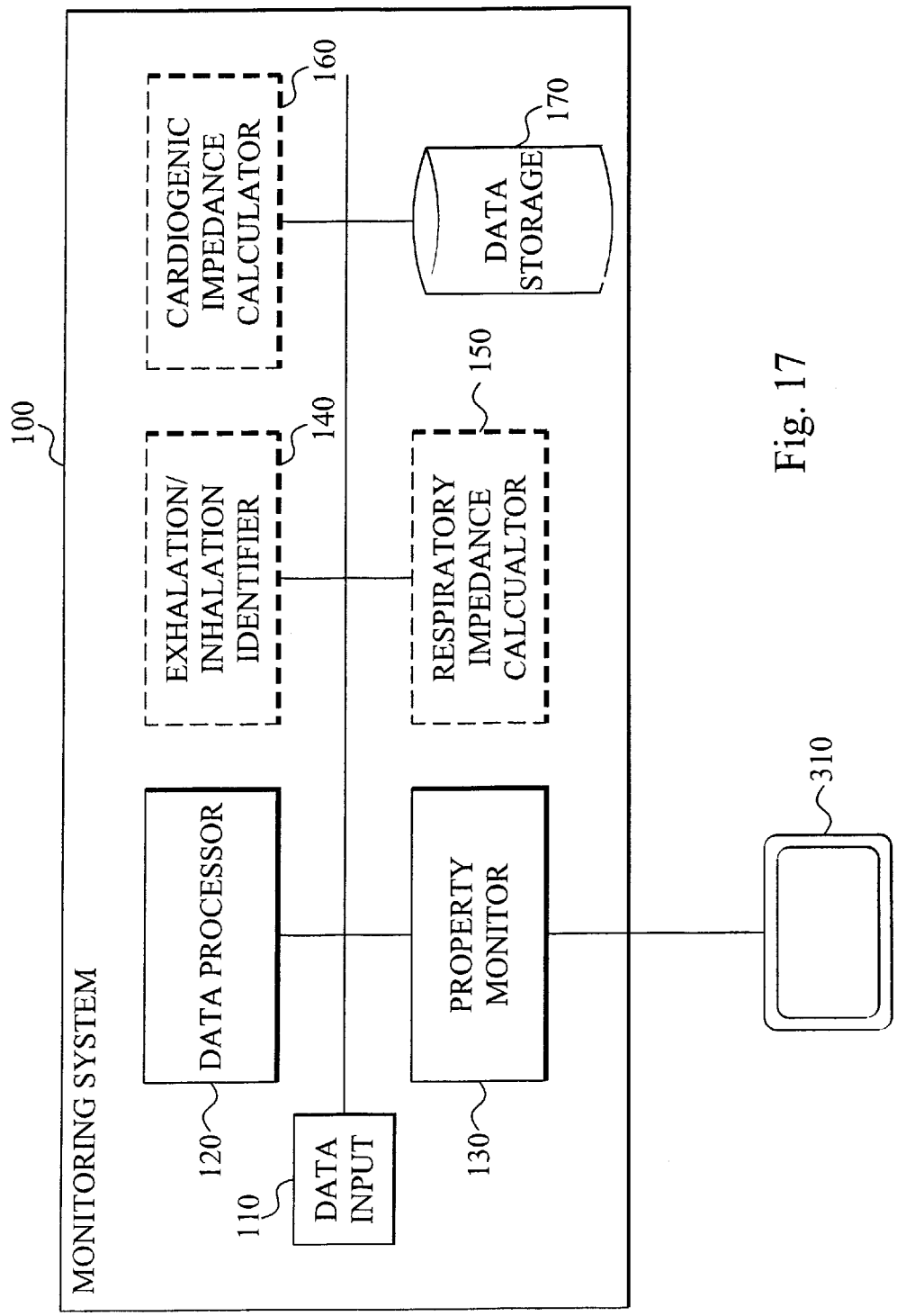
FIG. 17 is a schematic block diagram of a monitoring system according to the present invention.

FIG. 17 is a schematic block diagram of a monitoring system 100 according to an embodiment of the invention. The system 100 comprises a general data input 110 for receiving impedance-related data collected by the IMD. This input 110 could include a receiver chain of a wireless receiver, i.e. an antenna unit, demodulator and decoder. In such a case, the input data can be wirelessly transmitted from the IMD or an intermediate relay device to the system 100. In an alternative approach, the input 110 is adapted for receiving a data carrier, such as CD-disc, DVD-disc, USB-memory, etc. carrying the impedance related data. Also other inputs, e.g. network input, allowing a wired transmission of the data to the monitoring system 100 are possible.

The monitoring system 100 further comprises a data processor 120 arranged for generating a plurality of trend parameters. Each such trend parameter is obtained by collectively processing multiple cardiogenic impedance values reflective of the impedance of the heart in connection with an inhalation-to-exhalation transition and multiple impedance values reflective of the impedance of the heart in connection with an exhalation-to-inhalation transition.

The generated trend parameters are forwarded from the data processor 120 to a property monitor 130 of the system 100. This monitor 130 processes the received trend parameter for allowing a monitoring of the mechanical properties of the subject's heart. In a preferred implementation, this processing involves plotting the trend parameters versus recording time on a connected display screen 310. This display screen could then display any of the diagrams in FIG. 10, 11, 14 or 15 depending on the particular parameter type that is generated by the data processor 120 and the particular parameter processing conducted by the monitor 130.

A physician or even the patient himself/herself could view the screen and detect any change in the mechanical heart properties. This displayed data can constitute decision support information for the physician for determining the likelihood of a deleterious heart condition, such as ischemia, CHF, eminent hear attack, etc.

In a further implementation, the property monitor 130 instead or in addition sounds an alarm if there is a large change in the processed trend parameters. This could be an audio, tactile and/or visual alarm notifying the particular subject. The monitor 130 also or instead compiles an alarm message that is displayed on the screen 310, sent by a data output (not illustrated) to a handheld device carried by the subject, or sent by the data output to the subject's physician.

In an embodiment of the invention, the data received by the data input 110 is the desired cardiogenic impedance data collected by the IMD. In another embodiment, the input data is "raw" voltage/current data or partly processed such data. In such a case, the input data is forwarded from the input 110 to a calculator 160 arranged for calculating the desired cardiogenic impedance values. The calculator 160 generates the first and second impedance value sets that are subsequently used by the data processor 120 for generating the trend parameters.

In the case the input voltage/current data is not tagged for identifying whether the data is recorded in connection with a defined period of a heart cycle occurring in connection with an exhalation-to-inhalation or inhalation-to-exhalation transition in the respiratory cycle, the system 100 comprises and uses a transition identifier 140. This identifier 140 processes an input signal from the data input 110, such as pressure/sound recordings, IEGM recordings, respiratory impedance recordings, collected in the subject. The identifier 140 monitors the input signal for locating the time intervals corresponding to the transitions. As the input signal is preferably collected by the IMD, the signal can be time-marked with a same time reference as the voltage/current data. This allows the identifier 140 to correctly identify the correct voltage/current samples to be used by the calculator 160 when determining the cardiogenic impedance values.

In a preferred implementation, the system 150 comprises a calculator 150 for calculating the respiratory impedance from input voltage/current data. This calculator 150 and the cardiogenic impedance calculator 160 can be collectively implemented but equipped with different filters for discriminating between the impedance contribution from the respiratory system and from the cardiac system. In such a case, the calculated respiratory impedance signal is forwarded from the calculator 150 to the transition identifier 140. The identifier searches for peaks and valleys in the impedance signal, which correspond to the desired respiratory transitions.

The monitoring system 100 preferably also comprises a data storage 170 for, at least temporary, storing data received by the input 110 and processed by the different units 120 to 160 of the monitoring system 100. For example, calculated trend parameters from the data processor 120 can be entered in the data storage 170 and stored therein until a later review occasion. In such a case, the parameters are fetched from the storage 170 and brought to the property monitor 130 for display on the connected screen 310.

The units 110 to 160 of the monitoring system 100 may be provided as hardware, software or a combination of hardware and software. The monitoring system 100, or a least a portion of its included units 110 to 170, may be implemented in an IMD or an external device, preferably having capability of communicating with an IMD.

Figure 18:
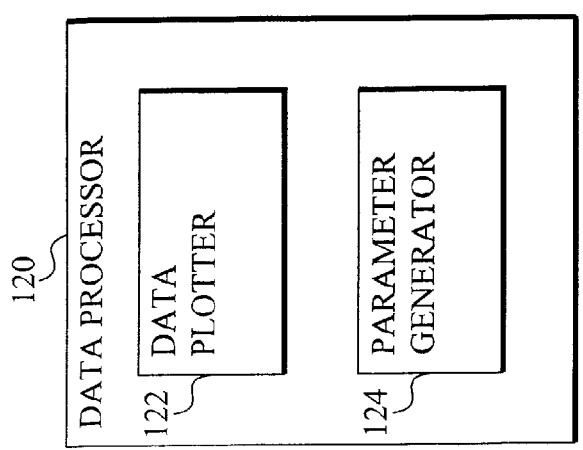
FIG. 18 is a schematic block diagram illustrating an embodiment of the data processor of FIG. 17 in more detail.

FIG. 18 is a schematic block diagram of an embodiment of the data processor 12 of FIG. 17. The data processor 120 comprises a data plotter 122 arranged for plotting the cardiogenic impedance values of the second value set as a function of the cardiogenic impedance values of the first set to form multiple plot points. These plot points are processed by a parameter generator 124 for generating a trend parameter. This generator 124 could for example be implemented for fitting an ellipse or a straight line to the multiple plot points. The generated trend parameter is then a parameter representative of the ellipse, such as major axis, angle, or the line, such as slope, correlation, MSE, as previously described.

The units 122 and 124 of the data processor 120 may be provided as hardware, software or a combination of hardware and software. The units 122 and 124 may all be implemented in the data processor 120. Alternatively, a distributed implementation with at least one of the units implemented in the monitoring system is also possible.

Figure 19:
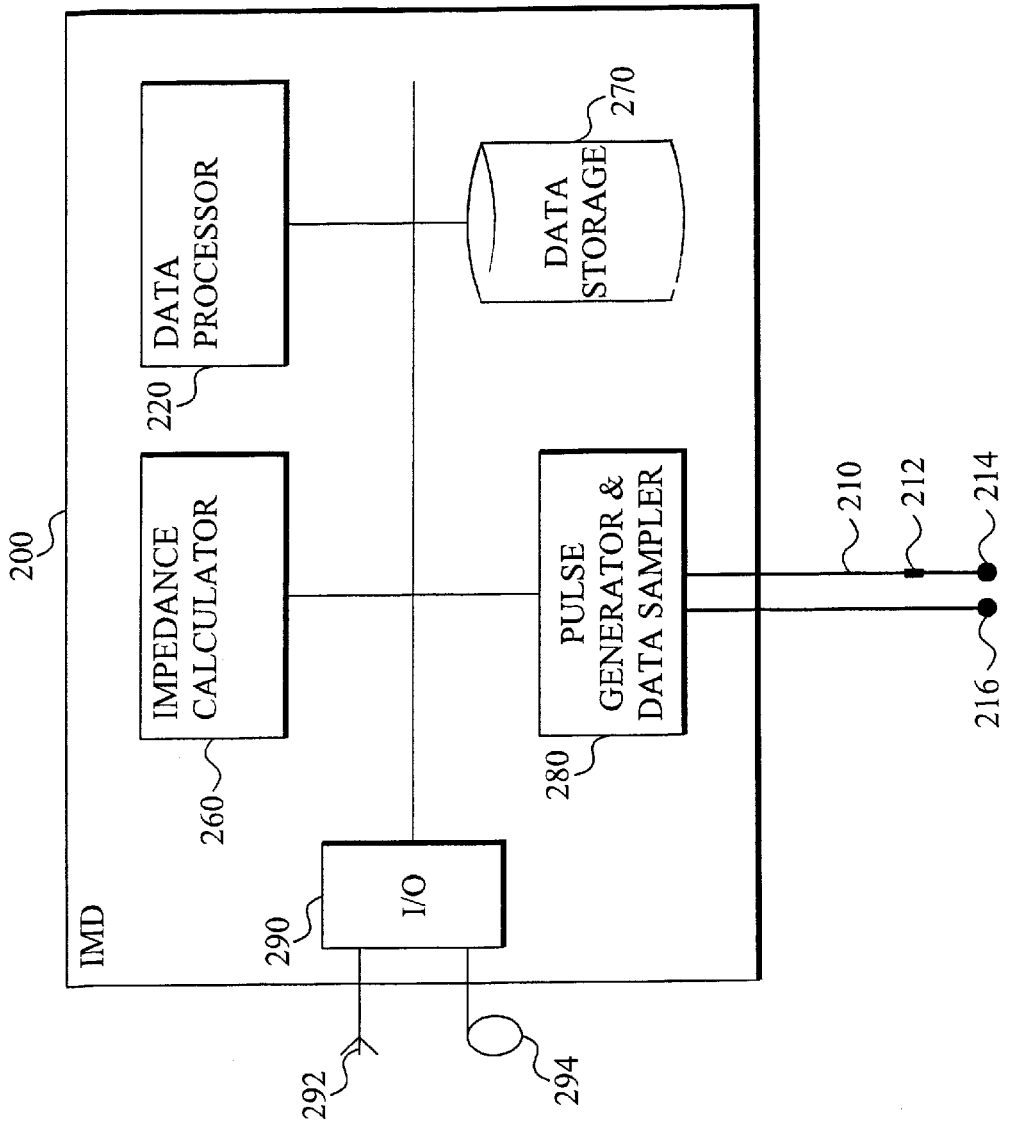
FIG. 19 is a schematic block diagram of an implantable medical device according to the present invention.

FIG. 19 is a schematic block diagram of an IMD 200 according to an embodiment of the present invention. The IMD 200 comprises a pulse generator and data sampler 280 having connected electrodes 212, 214, 216. This generator 280 is arranged for applying a current or voltage signal, preferably in the form of a train of current or voltage pulses, over two of the electrodes 212, 214. The resulting voltage or current signal is measured over two electrodes 214, 216 by a voltage or current measuring functionality of the generator/sampler 280. In the figure, the generator/sampler 280 is connected to two leads 210 equipped with the current/voltage electrodes 212, 214, 216. The number of used leads 210 (one or more) and electrodes 212, 214, 216 (two, three or four), the positioning of the electrodes 212, 214, 216 (RV, LV, RA, LA, epicardiac, intra-thoracic) and the types of electrodes 212, 214, 216 (tip, coil, ring) can be selected as previously described.

Information of the applied signal and the measured resulting signal is forwarded to an impedance calculator 260 of the IMD 200. This calculator 260 determines the first set of multiple cardiogenic impedance values and the second set of multiple cardiogenic impedance values per measured and monitored respiratory cycle. The two value sets are forwarded to a data processor 220 arranged for generating decision support information useful in monitoring the mechanical properties of the heart of the subject, in which the IMD 200 is implanted. This generation is performed by collectively processing the cardiogenic impedance values of the first and second set from the calculator 260. In a first embodiment, the processing involves tagging impedance values reflective of the impedance of the heart in connection with the previously described transitions in the respiratory cycle. In such a case, further data processing is required before the data can be used in the property monitoring of the invention. In a second embodiment, the processing involves generating a trend parameter that is reflective of the difference in cardiogenic impedance signal in the two transitions. This trend parameter is then used as decision support information, preferably accompanied with further such parameters recorded at other time intervals.

The generated decision support information can be forwarded to a data storage 270 for storage until a later retrieval. Upon data retrieval, the decision support information (trend parameter or tagged impedance data) is forwarded to an input and output (I/O) unit 290 (transmitter/receiver chain). This I/O unit 290 includes functionalities for processing incoming and outgoing data messages, optionally including modulator/demodulator and coder/decoder functionality. The I/O unit 290 is further preferably connected to an antenna arrangement 292 used for transmitting and receiving radio packets to and from the external unit, respectively. However, the I/O unit 290 could also or alternatively use other forms of wireless techniques than radio frequency transmissions when communicating with the external device. The I/O unit 290 could for example use an inductive antenna 294 for external wireless communication.

The I/O unit 290 compiles a message and transmits the decision support information to an external communications unit, such as a programmer or physician's workstation, preferably to a monitoring system of the invention implemented in this external unit.

In an alternative approach, the information forwarded from the generator/sampler 280 to the calculator 260 is directly forwarded to the I/O unit 290 for transmission to the external unit. In such a case, the monitoring system implemented in that unit includes an impedance calculator (see FIG. 17). Correspondingly, the impedance values calculated by the calculator 260 could be directly sent to the external unit via the I/O unit 290. The data processing functionality will then be conducted in the monitoring system of that unit.

The units 220, 260, 280 and 290 of the IMD 200 can be provided as hardware, software or a combination of hardware and software.

FIG. 20 is a schematic block diagram illustrating a possible implementation of the impedance calculator 260 of FIG. 19. This implementation could also be useful for the impedance calculator 160 of FIG. 17. In this calculator embodiment, a current signal (I) is applied over two electrodes and a resulting voltage signal (V) is measured. The measured AC voltage is optionally pre-amplified in an amplifier 261. The amplified voltage signal is forwarded to an integrator 262 basically arranged for calculating the voltage area of the signal per pulse. The integrator 262 also integrates the applied current signal for calculating the current area of the signal per pulse. The integrated absolute impedance can then be calculated in block 263 as the quotient between the voltage area and the current area. This raw impedance signal is input into two parallel filter chains. The first chain involves a bandpass filter 264 followed by a low-pass filter 265. The output from this filter chain is input to an analog to dialog (A/D) converter 268 to form the respiratory impedance signal $Z_r$. The second chain comprises a high-pass filter 266 followed by a low-pass filter 267. The filter output is processed through the A/D converted 268 to form the cardiogenic impedance signal $Z_c$. Thus, a same input "raw" signal can be used to obtain both the cardiogenic impedance signal, employed by the invention, and the respiratory impedance signal, useful for identifying correct portions in the cardiogenic signal, by different forms of filtering.

Figure 21:
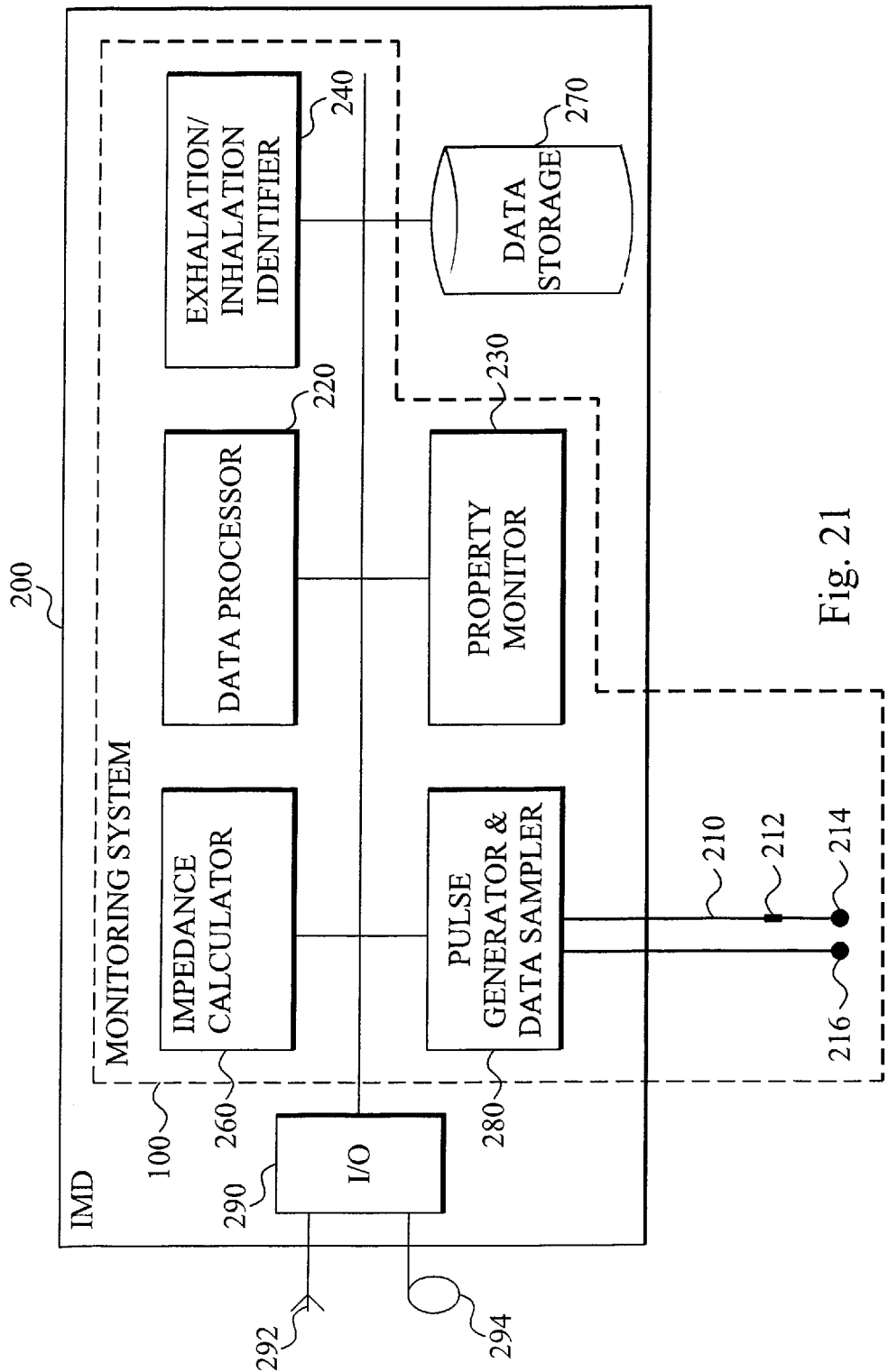
FIG. 21 is a schematic block diagram of an implantable medical device according to the present invention.

FIG. 21 is a schematic block diagram of another embodiment of an IMD 200 according to the invention. This IMD 200 comprises the monitoring system 100 of the invention used for generating a plurality of trend parameters. The operation of the units 220, 270, 280 and 290 is similar to what has previously described in connection with FIG. 19. Correspondingly, the operation of the transition identifier 240 is similar to what has been described in connection with FIG. 17. The property monitor 230 of the monitoring system 100 processes the trend parameters calculated by the data processor 220. The monitor 230 could for example time-stamp the different trend parameters or calculate average values from different sets of trend parameters. In a further embodiment, the property monitor 230 could monitor the different trend parameters to detect any sudden change in parameter values.

In such a case, the monitor 230 can generate an alarm message to be sent to an external device by the I/O unit 290.

The units 220, 230, 260, 280 and 290 of the IMD 200 can be provided as hardware, software or a combination of hardware and software.

Although modifications and changes may be suggested by those skilled in the art, it is the intention of the inventor to embody within the patent warranted heron all changes and modifications as reasonably and properly come within the scope of his or her contribution to the art.

I claim as my invention:

1. A method of monitoring mechanical properties of a heart in a subject, comprising the steps of:
   a) determining a first set of multiple cardiogenic impedance values reflective of the impedance of said heart during a defined period of a heart cycle occurring in connection with a transition from inhalation to exhalation in said subject;
   b) determining a second set of multiple cardiogenic impedance values reflective of the impedance of said heart during said defined period of a heart cycle occurring in connection with a transition from exhalation to inhalation in said subject;
   c) collectively processing with a data processor said multiple cardiogenic impedance values of said first set as a function of said second set to determine a relationship between the first and second set and analyzing the relationship between the first and second sets to form a trend parameter representative of respiratory effect on said cardiogenic impedance values;
   d) repeating said determining steps a), b) and processing step c) to form a plurality of trend parameters over time; and
   e) monitoring said mechanical properties of said heart by processing said plurality of trend parameters.

2. The method according to claim 1, wherein step a) comprises:
   applying a first current signal or a first voltage signal to at least a portion of said heart during a first portion of a respiratory cycle;
   measuring a first resulting voltage signal or a first resulting current signal over at least a portion of said heart during said first portion of said respiratory cycle; and
   generating said first set of multiple cardiogenic impedance values based on said first current signal and said first resulting voltage signal or said first voltage signal and said first resulting current signal; and wherein step b) comprises: applying a second current signal or a second voltage signal to at least a portion of said heart during a second portion of said respiratory cycle; measuring a second resulting voltage signal or a second resulting current signal over at least a portion of said heart during said second portion of said respiratory cycle; and generating said second set of multiple cardiogenic impedance values based on said second current signal and said second resulting voltage signal or said second voltage signal and said second resulting current signal.

3. The method according to claim 1, wherein step c) comprises the steps of: plotting said multiple cardiogenic impedance values of said second set as a function of said multiple cardiogenic impedance values of said first set to obtain multiple plot points; and generating said trend parameter by processing said multiple plot points.

4. The method according to claim 3, wherein said generating step comprises the steps of: fitting an ellipse to said multiple plot points; and generating said trend parameter as a parameter being representative of said ellipse.

5. The method according to claim 3, wherein said generating step comprises the steps of: fitting a straight line to said multiple plot points; generating said trend parameter as a parameter being representative of said straight line.

6. The method according to claim 1, wherein step e) comprises plotting said plurality of trend parameters to display any changes of said mechanical properties of said heart.

7. The method according to claim 6, wherein said changes of said mechanical properties are due to an ischemic heart disease, progression of heart failure or poor inter-chamber synchronization of said heart.

8. A method of monitoring mechanical properties of a heart in a subject, comprising the steps of:
   a) determining a first set of multiple cardiogenic impedance values reflective of the impedance of said heart in connection with a transition from inhalation to exhalation in said subject;
   b) determining a second set of multiple cardiogenic impedance values reflective of the impedance of said heart in connection with a transition from exhalation to inhalation in said subject:
   c) collectively processing with a data processor said multiple cardiogenic impedance values of said first set as a function of said second set to determine a relationship between the first and second set and analyzing the relationship between the first and second sets to form a trend parameter representative of respiratory effect on said cardiogenic impedance values;
   d) repeating said determining steps a), b) and processing step c) to form a plurality of trend parameters over time;
   e) monitoring said mechanical properties of said heart by processing said plurality of trend parameters;
   f) identifying a first heart cycle occurring in connection with said transition from inhalation to exhalation; and
   g) identifying a second heart cycle occurring in connection with said transition from exhalation to inhalation; and wherein step a) comprises determining multiple cardiogenic impedance values reflective of the impedance of said heart during at least a portion said first heart cycle, and wherein step b) comprises determining multiple cardiogenic impedance values reflective of the impedance of said heart during at least a portion of said second heart cycle.

9. The method according to claim 8, further comprising the step of:
   h) generating a signal of multiple respiratory impedance values of said subject; and wherein step f) comprises identifying said first heart cycle as a heart cycle occurring in connection with a maximum value of said respiratory impedance signal during a respiration cycle, and wherein step g) comprises identifying said second heart cycle as a heart cycle occurring in connection with a minimum value of said respiratory impedance signal during said respiration cycle.

10. The method according to claim 9, wherein step f) comprises identifying said first heart cycle as a heart cycle coinciding with or being closest in time to said maximum value of said respiratory impedance signal during said respiration cycle and wherein step g) comprises identifying said second heart cycle as a heart cycle coinciding with or being closest in time to said minimum value of said respiratory impedance signal during said respiration cycle.

11. A system for monitoring mechanical properties of a heart in a subject, said system comprising:

a data processor that generates a plurality of trend parameters representative of respiratory effect on cardiogenic impedance values by, for each trend parameter, collectively processing multiple cardiogenic impedance values reflective of the impedance of said heart during a defined period of a heart cycle occurring in connection with a transition from inhalation to exhalation in said subject as a function of multiple cardiogenic impedance values reflective of the impedance of said heart during said defined period of a heart cycle occurring in connection with a transition from exhalation to inhalation in said subject to determine a relationship between the first and second set and analyzing the relationship between the first and second sets to form the trend parameters; and a property monitor that monitors said mechanical properties of said heart by processing said plurality of trend parameters.

12. The system according to claim 11, wherein the data processor is adapted to generate a plurality of first sets, each first set comprising multiple cardiogenic impedance values reflective of the impedance of said heart in connection with said transition from inhalation to exhalation in said subject, the data processor being further adapted to determine a plurality of second sets, each second set comprising multiple cardiogenic impedance values reflective of the impedance of said heart in connection with said transition from exhalation to inhalation of said subject.

13. The system according to claim 12, further comprising: a current applier that applies a current signal or a voltage signal to at least a portion of said heart; and a voltage measurer that measures a resulting voltage signal or a resulting current signal over at least a portion of said heart, and wherein said data processor generates multiple cardiogenic impedance values based on said current signal and said resulting voltage signal or said voltage signal and said resulting current signal.

14. The system according to claim 11, wherein said data processor comprises: a data plotter that plots said multiple cardiogenic impedance values reflective of the impedance of said heart in connection with said transition from exhalation to inhalation as a function of said multiple impedance values reflective of the cardiogenic impedance of said heart in connection with said transition from inhalation to exhalation to obtain multiple plot points; and a parameter generator that generates a trend parameter by processing said multiple plot points.

15. The system according to claim 14, wherein said parameter generator i) fits an ellipse to said multiple plot points and ii) generates said trend parameter as a parameter being representative of said ellipse.

16. The system according to claim 14, wherein said parameter generator fits a straight line to said multiple plot points and ii) generates said trend parameter as a parameter being representative of said straight line.

17. The system according to claim 11, wherein said property monitor plots said plurality of trend parameters on a connected display screen to display any changes of said mechanical properties of said heart.

18. A system for monitoring mechanical properties of a heart in a subject, said system comprising:
a data processor that generates a plurality of trend parameters representative of respiratory effect on cardiogenic impedance values by, for each trend parameter, collectively processing multiple cardiogenic impedance values reflective of the impedance of said heart in connection with a transition from inhalation to exhalation in said subject as a function of multiple cardiogenic impedance values reflective of the impedance of said heart in connection with a transition from exhalation to inhalation in said subject to determine a relationship between the first and second set and analyzing the relationship between the first and second sets to form the trend parameters;

a property monitor that monitors said mechanical properties of said heart by processing said plurality of trend parameters;

an identification unit that i) identifies, for each first set, a first heart cycle of a respiratory cycle occurring in connection with said transition from inhalation to exhalation and ii) identifies, for each second set, a second heart cycle of said respiratory cycle occurring in connection with said transition from exhalation to inhalation.

19. The system according to claim 18, wherein said data processor i) determines, for each first set, multiple cardiogenic impedance values reflective of the impedance of said heart during at least a portion of said first heart cycle, and ii) determines, for each second set, said multiple cardiogenic impedance values reflective of the impedance of said heart during at least a portion of said second heart cycle.

20. The system according to claim 19, further comprising a signal generator adapted to generate a signal of multiple respiratory impedance values of said subject, and an identification unit adapted to identify for each first set, said first heart cycle as a heart cycle occurring in connection with a maximum value of said respiratory impedance signal during a respiration cycle, and for each second set, said second heart cycle as a heart cycle occurring in connection with a minimum value of said respiratory impedance signal during said respiration cycle.

21. The system according to claim 20, wherein said identification unit i) identifies, for each first set, said first heart cycle as a heart cycle coinciding with or being closest in time to said maximum value of said respiratory impedance signal during said respiration cycle and ii) identifies, for each second set, second heart cycle as a heart cycle coinciding with or being closest in time to said minimum value of said respiratory impedance signal during said respiration cycle.

22. An implantable medical device comprising: a system that i) determines a first set of multiple cardiogenic impedance values reflective of the impedance of a heart during a defined period of a heart cycle occurring in a subject in connection with a transition from inhalation to exhalation in said subject, and ii) determines a second set of multiple cardiogenic impedance values reflective of the impedance of said heart during said defined period of a heart cycle occurring in connection with a transition from exhalation to inhalation of said subject; and a data processor that generates decision support information useful in monitoring mechanical properties of said heart by collectively processing said first set of multiple cardiogenic impedance values as a function of said second set of multiple cardiogenic impedance values to determine a relationship between the first and second set and analyzing the relationship between the first and second sets to form the trend parameters.

* * * * *